US008034090B2

(12) United States Patent
Stone et al.

(10) Patent No.: US 8,034,090 B2
(45) Date of Patent: Oct. 11, 2011

(54) TISSUE FIXATION DEVICE

(75) Inventors: Kevin T. Stone, Winona Lake, IN (US);
H. Gene Hawkins, Warsaw, IN (US);
Zachary M. Hoffman, Warsaw, IN
(US); Gregory J. Denham, Warsaw, IN
(US); Troy M. Walters, Plymouth, IN
(US); Ryan A. Kaiser, Leesburg, IN
(US); Jason D. Meridew, Syracuse, IN
(US)

(73) Assignee: Biomet Sports Medicine, LLC, Warsaw, IN (US)

( * ) Notice: Subject to any disclaimer, the term of this patent is extended or adjusted under 35 U.S.C. 154(b) by 1356 days.

(21) Appl. No.: 11/386,071

(22) Filed: Mar. 21, 2006

(65) Prior Publication Data
US 2006/0247642 A1    Nov. 2, 2006

Related U.S. Application Data

(63) Continuation-in-part of application No. 11/294,694, filed on Dec. 5, 2005, now Pat. No. 7,914,539, which is a continuation-in-part of application No. 10/984,624, filed on Nov. 9, 2004, now Pat. No. 7,608,098.

(51) Int. Cl.
*A61F 2/08* (2006.01)
*A31B 17/04* (2006.01)
(52) U.S. Cl. ............. 606/321; 606/300; 623/13.11; 623/13.14
(58) Field of Classification Search ........... 623/11.11, 623/13.11–13.2; 606/300–321
See application file for complete search history.

(56) References Cited

U.S. PATENT DOCUMENTS

| 26,501 | A | 10/1859 | Kendrick et al. |
| 126,366 | A | 4/1872 | Wills |
| 233,475 | A | 10/1880 | Cook et al. |
| 261,501 | A | 7/1882 | Vandermark |
| 417,805 | A | 12/1889 | Beaman |
| 487,304 | A | 12/1892 | Todd |
| 837,767 | A | 12/1906 | Aims |
| 1,059,631 | A | 4/1913 | Popovics |
| 1,131,155 | A | 3/1915 | Murphy |

(Continued)

FOREIGN PATENT DOCUMENTS
AU      49572/64       3/1966
(Continued)

OTHER PUBLICATIONS

Arthrotek, A Biomet Company; Knees; Sure fire Hybrid Meniscal Device.

(Continued)

*Primary Examiner* — Thomas C Barrett
*Assistant Examiner* — Matthew Lawson
(74) *Attorney, Agent, or Firm* — Harness, Dickey

(57) ABSTRACT

A method for securing a graft to a bone includes forming a tunnel in the bone, positioning the graft in the tunnel, and securing the graft in the tunnel with an anchor. The method also includes attaching a distal end of an elongated anchor sleeve to a proximal end of the anchor and inserting a pre-compressed harvested bone material having a cruciate cross-section through the anchor sleeve into to a bore defined in the anchor. The bore has a mating cruciate cross-section. The method also includes removing the anchor sleeve after inserting the bone material into the anchor.

18 Claims, 27 Drawing Sheets

U.S. PATENT DOCUMENTS

| | | | |
|---|---|---|---|
| 1,153,450 A | 9/1915 | Schaff |
| 1,635,066 A | 7/1927 | Wells |
| 2,012,776 A | 8/1935 | Roeder |
| 2,065,659 A | 12/1936 | Cullen |
| 2,108,206 A | 2/1938 | Meeker |
| 2,242,003 A | 5/1941 | Lorenzo |
| 2,302,986 A | 11/1942 | Vollrath |
| 2,397,216 A | 3/1946 | Stellin |
| RE22,857 E | 3/1947 | Ogburn |
| 2,526,959 A | 10/1950 | Lorenzo |
| 2,562,419 A | 7/1951 | Ferris |
| 2,581,564 A | 1/1952 | Villegas |
| 2,610,631 A | 9/1952 | Calicchio |
| 2,669,774 A | 2/1954 | Mitchell |
| 2,760,488 A | 8/1956 | Pierce |
| 2,833,284 A | 5/1958 | Springer |
| 2,846,712 A | 8/1958 | Markman |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,013,559 A | 12/1961 | Thomas |
| 3,037,619 A | 6/1962 | Stevens |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,240,379 A | 3/1966 | Bremer et al. |
| 3,399,432 A | 9/1968 | Merser |
| RE26,501 E | 12/1968 | Kendrick et al. |
| 3,470,834 A | 10/1969 | Bone |
| 3,470,875 A | 10/1969 | Johnson |
| 3,500,820 A | 3/1970 | Almen |
| 3,515,132 A | 6/1970 | McKnight |
| 3,527,223 A | 9/1970 | Shein |
| 3,541,591 A | 11/1970 | Hoegerman |
| 3,547,389 A | 12/1970 | Mitchell |
| 3,579,831 A | 5/1971 | Stevens |
| 3,618,447 A | 11/1971 | Goins |
| 3,643,649 A | 2/1972 | Amato |
| 3,664,345 A | 5/1972 | Dabbs et al. |
| 3,675,639 A | 7/1972 | Cimber |
| 3,695,271 A | 10/1972 | Chodorow |
| 3,699,969 A | 10/1972 | Allen |
| 3,716,058 A | 2/1973 | Tanner, Jr. |
| 3,752,516 A | 8/1973 | Mumma |
| 3,757,629 A | 9/1973 | Schneider |
| 3,807,407 A | 4/1974 | Schweizer |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,907,442 A | 9/1975 | Reid |
| 3,910,281 A | 10/1975 | Kletschka et al. |
| 3,931,667 A | 1/1976 | Merser et al. |
| 3,943,932 A | 3/1976 | Woo |
| 3,946,740 A | 3/1976 | Bassett |
| 3,954,103 A | 5/1976 | Garcia-Roel et al. |
| 3,961,632 A | 6/1976 | Moossun |
| 3,976,079 A | 8/1976 | Samuels et al. |
| 3,977,050 A | 8/1976 | Perez |
| 3,979,799 A | 9/1976 | Merser et al. |
| 3,985,138 A | 10/1976 | Jarvik |
| 3,990,619 A | 11/1976 | Russell |
| 4,006,747 A | 2/1977 | Kronenthal et al. |
| 4,007,743 A | 2/1977 | Blake |
| 4,013,071 A | 3/1977 | Rosenberg et al. |
| 4,094,313 A | 6/1978 | Komamura et al. |
| 4,103,690 A | 8/1978 | Harris |
| RE29,819 E | 10/1978 | Bone |
| 4,121,487 A | 10/1978 | Bone |
| 4,144,876 A | 3/1979 | DeLeo |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,275,717 A | 6/1981 | Bolesky |
| 4,287,807 A | 9/1981 | Pacharis et al. |
| 4,291,698 A | 9/1981 | Fuchs et al. |
| 4,312,337 A | 1/1982 | Donohue |
| 4,316,469 A | 2/1982 | Kapitanov |
| 4,326,531 A | 4/1982 | Shimonaka |
| 4,345,601 A | 8/1982 | Fukuda |
| 4,349,027 A | 9/1982 | DiFrancesco |
| 4,402,445 A | 9/1983 | Green |
| 4,409,974 A | 10/1983 | Freedland |
| 4,438,769 A | 3/1984 | Pratt et al. |
| 4,454,875 A | 6/1984 | Pratt et al. |
| 4,462,395 A | 7/1984 | Johnson |
| 4,463,753 A | 8/1984 | Gustilo |
| 4,484,570 A | 11/1984 | Sutter et al. |
| 4,493,323 A | 1/1985 | Albright et al. |
| 4,505,274 A | 3/1985 | Speelman |
| 4,531,522 A | 7/1985 | Bedi et al. |
| 4,534,350 A | 8/1985 | Golden et al. |
| 4,537,185 A | 8/1985 | Stednitz |
| 4,561,432 A | 12/1985 | Mazor |
| 4,570,623 A | 2/1986 | Ellison et al. |
| 4,590,928 A | 5/1986 | Hunt et al. |
| 4,595,007 A | 6/1986 | Mericle |
| 4,596,249 A | 6/1986 | Freda et al. |
| 4,602,635 A | 7/1986 | Mulhollan et al. |
| 4,602,636 A | 7/1986 | Noiles |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,653,487 A | 3/1987 | Maale |
| 4,653,489 A | 3/1987 | Tronzo |
| 4,662,068 A | 5/1987 | Polonsky |
| 4,667,675 A | 5/1987 | Davis |
| 4,669,473 A | 6/1987 | Richards et al. |
| 4,683,895 A | 8/1987 | Pohndorf |
| 4,705,040 A | 11/1987 | Mueller et al. |
| 4,716,893 A | 1/1988 | Fischer et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,738,255 A | 4/1988 | Goble et al. |
| 4,741,330 A | 5/1988 | Hayhurst |
| 4,741,336 A | 5/1988 | Failla et al. |
| 4,750,492 A | 6/1988 | Jacobs |
| 4,760,843 A | 8/1988 | Fischer et al. |
| 4,772,261 A | 9/1988 | Von Hoff et al. |
| 4,776,328 A | 10/1988 | Frey et al. |
| 4,781,190 A | 11/1988 | Lee |
| 4,784,126 A | 11/1988 | Hourahane et al. |
| 4,787,882 A | 11/1988 | Clarén |
| 4,790,297 A | 12/1988 | Luque |
| 4,809,695 A | 3/1989 | Gwathmey et al. |
| 4,823,794 A | 4/1989 | Pierce |
| 4,832,026 A | 5/1989 | Jones |
| 4,834,098 A | 5/1989 | Jones |
| 4,841,960 A | 6/1989 | Garner |
| 4,858,608 A | 8/1989 | McQuilkin |
| 4,860,513 A | 8/1989 | Whitman |
| 4,870,957 A | 10/1989 | Goble et al. |
| 4,873,976 A | 10/1989 | Schreiber |

| | | | | | | |
|---|---|---|---|---|---|---|
| 4,887,601 A | 12/1989 | Richards | | 5,437,680 A | 8/1995 | Yoon |
| 4,890,615 A | 1/1990 | Caspari et al. | | 5,439,684 A | 8/1995 | Prewett et al. |
| 4,893,974 A | 1/1990 | Fischer et al. | | 5,443,509 A | 8/1995 | Boucher et al. |
| 4,895,148 A | 1/1990 | Bays et al. | | 5,447,512 A | 9/1995 | Wilson et al. |
| 4,896,668 A | 1/1990 | Popoff et al. | | 5,456,685 A | 10/1995 | Huebner |
| 4,898,156 A | 2/1990 | Gatturna et al. | | 5,466,237 A | 11/1995 | Byrd, III et al. |
| 4,901,721 A | 2/1990 | Hakki | | 5,467,786 A | 11/1995 | Allen et al. |
| 4,923,461 A | 5/1990 | Caspari et al. | | 5,470,334 A | 11/1995 | Ross et al. |
| 4,927,421 A | 5/1990 | Goble et al. | | 5,470,337 A | 11/1995 | Moss |
| 4,946,468 A | 8/1990 | Li | | 5,474,572 A | 12/1995 | Hayhurst |
| 4,950,285 A | 8/1990 | Wilk | | 5,484,442 A | 1/1996 | Melker et al. |
| 4,960,381 A | 10/1990 | Niznick | | 5,490,750 A | 2/1996 | Gundy |
| 4,961,741 A | 10/1990 | Hayhurst | | 5,496,331 A | 3/1996 | Xu et al. |
| 4,968,315 A | 11/1990 | Gatturna | | 5,505,736 A | 4/1996 | Reimels et al. |
| 4,968,317 A | 11/1990 | Törmälä et al. | | 5,520,691 A | 5/1996 | Branch |
| 4,976,736 A | 12/1990 | White et al. | | 5,522,820 A | 6/1996 | Caspari et al. |
| 4,978,350 A | 12/1990 | Wagenknecht | | 5,522,846 A | 6/1996 | Bonutti |
| 4,983,176 A | 1/1991 | Cushman et al. | | 5,527,342 A | 6/1996 | Pietrzak et al. |
| 5,002,562 A | 3/1991 | Oberlander | | 5,527,343 A | 6/1996 | Bonutti |
| 5,041,129 A | 8/1991 | Hayhurst et al. | | 5,545,178 A | 8/1996 | Kensey et al. |
| 5,047,030 A | 9/1991 | Draenert | | 5,545,228 A | 8/1996 | Kambin |
| 5,053,046 A | 10/1991 | Janese | | 5,549,630 A | 8/1996 | Bonutti |
| 5,053,047 A | 10/1991 | Yoon | | 5,549,631 A | 8/1996 | Bonutti |
| 5,059,201 A | 10/1991 | Asnis | | 5,571,139 A | 11/1996 | Jenkins, Jr. |
| 5,059,206 A | 10/1991 | Winters | | 5,573,286 A | 11/1996 | Rogozinski |
| 5,080,050 A | 1/1992 | Dale | | 5,573,548 A | 11/1996 | Nazre et al. |
| 5,084,050 A * | 1/1992 | Draenert ................ 606/77 | | 5,584,862 A | 12/1996 | Bonutti |
| 5,084,058 A | 1/1992 | Li | | 5,591,207 A | 1/1997 | Coleman |
| 5,085,661 A | 2/1992 | Moss | | 5,593,407 A | 1/1997 | Reis |
| 5,087,263 A | 2/1992 | Li | | 5,601,557 A | 2/1997 | Hayhurst |
| 5,098,435 A | 3/1992 | Stednitz et al. | | 5,601,559 A | 2/1997 | Melker et al. |
| 5,123,913 A | 6/1992 | Wilk et al. | | 5,601,571 A | 2/1997 | Moss |
| 5,129,901 A | 7/1992 | Decoste | | 5,641,256 A | 6/1997 | Gundy |
| 5,129,904 A | 7/1992 | Illi | | 5,643,269 A | 7/1997 | Härle |
| 5,139,499 A | 8/1992 | Small et al. | | 5,643,320 A | 7/1997 | Lower et al. |
| 5,143,498 A | 9/1992 | Whitman | | 5,645,546 A | 7/1997 | Fard |
| 5,149,329 A | 9/1992 | Richardson | | 5,645,547 A | 7/1997 | Coleman |
| 5,152,790 A | 10/1992 | Rosenberg et al. | | 5,647,874 A | 7/1997 | Hayhurst |
| 5,154,189 A | 10/1992 | Oberlander | | 5,658,289 A * | 8/1997 | Boucher et al. ............ 623/13.14 |
| 5,156,616 A | 10/1992 | Meadows et al. | | 5,658,299 A | 8/1997 | Hart |
| 5,169,400 A | 12/1992 | Mühling et al. | | 5,658,313 A | 8/1997 | Thal |
| 5,176,682 A | 1/1993 | Chow | | 5,665,112 A | 9/1997 | Thal |
| 5,178,629 A | 1/1993 | Kammerer | | 5,679,723 A | 10/1997 | Cooper et al. |
| 5,192,282 A | 3/1993 | Draenert | | 5,683,419 A | 11/1997 | Thal |
| 5,203,784 A | 4/1993 | Ross et al. | | 5,688,285 A | 11/1997 | Yamada |
| 5,203,787 A | 4/1993 | Noblitt et al. | | 5,690,678 A | 11/1997 | Johnson |
| 5,209,805 A | 5/1993 | Spraggins | | 5,695,497 A | 12/1997 | Stahelin |
| 5,211,647 A | 5/1993 | Schmieding | | 5,697,929 A | 12/1997 | Mellinger |
| 5,211,650 A | 5/1993 | Noda | | 5,702,397 A | 12/1997 | Goble et al. |
| 5,214,987 A | 6/1993 | Fenton, Sr. | | 5,702,462 A | 12/1997 | Oberlander |
| 5,242,447 A | 9/1993 | Borzone | | 5,707,373 A | 1/1998 | Sevrain et al. |
| 5,249,899 A | 10/1993 | Wilson | | 5,713,904 A | 2/1998 | Errico et al. |
| 5,258,015 A | 11/1993 | Li et al. | | 5,716,359 A | 2/1998 | Ojima et al. |
| 5,269,160 A | 12/1993 | Wood | | 5,718,717 A | 2/1998 | Bonutti |
| 5,269,783 A | 12/1993 | Sander | | 5,720,765 A | 2/1998 | Thal |
| 5,269,809 A | 12/1993 | Hayhurst et al. | | 5,725,549 A | 3/1998 | Lam |
| 5,282,809 A | 2/1994 | Kammerer et al. | | 5,725,556 A | 3/1998 | Moser et al. |
| 5,312,438 A | 5/1994 | Johnson | | 5,725,581 A | 3/1998 | Branemark |
| 5,318,577 A | 6/1994 | Li | | 5,728,109 A | 3/1998 | Schulze et al. |
| 5,318,578 A | 6/1994 | Hasson | | 5,728,136 A | 3/1998 | Thal |
| 5,320,633 A | 6/1994 | Allen et al. | | 5,733,306 A | 3/1998 | Bonutti |
| 5,334,204 A | 8/1994 | Clewett et al. | | 5,743,912 A | 4/1998 | Lahille et al. |
| 5,336,229 A | 8/1994 | Noda | | 5,746,754 A | 5/1998 | Chan |
| 5,336,231 A | 8/1994 | Adair | | 5,749,898 A | 5/1998 | Schulze et al. |
| 5,336,240 A | 8/1994 | Metzler et al. | | 5,766,176 A | 6/1998 | Duncan |
| 5,342,369 A | 8/1994 | Harryman, II | | 5,769,899 A * | 6/1998 | Schwartz et al. ................ 606/77 |
| 5,358,511 A | 10/1994 | Gatturna et al. | | 5,776,196 A | 7/1998 | Matsuzaki et al. |
| 5,360,431 A | 11/1994 | Puno et al. | | 5,782,864 A | 7/1998 | Lizardi |
| 5,364,400 A | 11/1994 | Rego, Jr. et al. | | 5,792,142 A | 8/1998 | Galitzer |
| 5,374,268 A | 12/1994 | Sander | | 5,796,127 A | 8/1998 | Hayafuji et al. |
| 5,383,878 A | 1/1995 | Roger et al. | | 5,797,928 A | 8/1998 | Kogasaka |
| 5,391,171 A | 2/1995 | Schmieding | | 5,800,407 A | 9/1998 | Eldor |
| RE34,871 E | 3/1995 | McGuire et al. | | 5,810,848 A | 9/1998 | Hayhurst |
| 5,397,356 A | 3/1995 | Goble et al. | | 5,814,069 A | 9/1998 | Schulze et al. |
| 5,403,348 A | 4/1995 | Bonutti | | 5,814,070 A | 9/1998 | Borzone et al. |
| 5,417,691 A | 5/1995 | Hayhurst | | 5,843,084 A | 12/1998 | Hart et al. |
| 5,423,819 A | 6/1995 | Small et al. | | 5,846,254 A | 12/1998 | Schulze et al. |
| 5,425,766 A | 6/1995 | Bowald | | 5,860,973 A | 1/1999 | Michelson |
| 5,433,751 A | 7/1995 | Christel et al. | | 5,868,740 A | 2/1999 | LeVeen et al. |

| | | | | | | |
|---|---|---|---|---|---|---|
| 5,871,484 | A | 2/1999 | Spievack et al. | 6,387,129 | B2 | 5/2002 | Rieser et al. |
| 5,871,486 | A | 2/1999 | Huebner et al. | 6,398,785 | B2 | 6/2002 | Carchidi et al. |
| 5,871,490 | A | 2/1999 | Schulze et al. | 6,409,743 | B1 | 6/2002 | Fenton, Jr. |
| 5,891,168 | A | 4/1999 | Thal | 6,413,260 | B1 | 7/2002 | Berrevoets et al. |
| 5,893,592 | A | 4/1999 | Schulze et al. | 6,423,088 | B1 | 7/2002 | Fenton, Jr. |
| 5,895,395 | A | 4/1999 | Yeung | 6,428,562 | B2 | 8/2002 | Bonutti |
| 5,897,564 | A | 4/1999 | Schulze et al. | 6,432,123 | B2 | 8/2002 | Schwartz et al. |
| 5,899,902 | A | 5/1999 | Brown et al. | 6,440,136 | B1 | 8/2002 | Gambale et al. |
| 5,941,439 | A | 8/1999 | Kammerer et al. | 6,454,768 | B1 | 9/2002 | Jackson |
| 5,946,783 | A | 9/1999 | Plociennik et al. | 6,458,134 | B1 | 10/2002 | Songer et al. |
| 5,948,002 | A | 9/1999 | Bonutti | 6,461,373 | B2 | 10/2002 | Wyman et al. |
| 5,951,560 | A | 9/1999 | Simon et al. | 6,464,713 | B2 | 10/2002 | Bonutti |
| 5,954,747 | A | 9/1999 | Clark | 6,468,293 | B2 | 10/2002 | Bonutti et al. |
| 5,961,524 | A | 10/1999 | Crombie | 6,471,707 | B1 | 10/2002 | Miller et al. |
| 5,964,767 | A | 10/1999 | Tapia et al. | 6,475,230 | B1 | 11/2002 | Bonutti et al. |
| 5,964,783 | A | 10/1999 | Grafton et al. | 6,497,901 | B1 | 12/2002 | Royer |
| 5,968,045 | A | 10/1999 | Frazier | 6,500,184 | B1 | 12/2002 | Chan et al. |
| 5,968,047 | A | 10/1999 | Reed | 6,500,195 | B2 | 12/2002 | Bonutti |
| 5,976,127 | A | 11/1999 | Lax | RE37,963 | E | 1/2003 | Thai |
| 5,980,524 | A | 11/1999 | Justin et al. | 6,508,820 | B2 | 1/2003 | Bales |
| 5,980,558 | A | 11/1999 | Wiley | 6,508,821 | B1 | 1/2003 | Schwartz et al. |
| 5,980,559 | A | 11/1999 | Bonutti | 6,511,498 | B1 | 1/2003 | Fumex |
| 5,989,252 | A | 11/1999 | Fumex | 6,517,542 | B1 | 2/2003 | Papay et al. |
| 5,989,256 | A | 11/1999 | Kuslich et al. | 6,517,579 | B1 | 2/2003 | Paulos et al. |
| 5,997,542 | A | 12/1999 | Burke | 6,520,964 | B2 | 2/2003 | Tallarida et al. |
| 5,997,552 | A | 12/1999 | Person et al. | 6,527,777 | B2 | 3/2003 | Justin |
| 6,001,100 | A | 12/1999 | Sherman et al. | 6,527,794 | B1 | 3/2003 | McDevitt et al. |
| 6,010,525 | A | 1/2000 | Bonutti et al. | 6,537,319 | B2 | 3/2003 | Whelan |
| 6,016,727 | A | 1/2000 | Morgan | 6,540,770 | B1 | 4/2003 | Tornier et al. |
| 6,022,352 | A | 2/2000 | Vandewalle | 6,547,564 | B1 | 4/2003 | Hansson |
| 6,022,373 | A | 2/2000 | Li | 6,551,343 | B1 | 4/2003 | Tormala et al. |
| 6,024,758 | A | 2/2000 | Thal | 6,554,830 | B1 | 4/2003 | Chappius |
| 6,039,753 | A | 3/2000 | Meislin | 6,554,852 | B1 | 4/2003 | Oberlander |
| 6,045,574 | A | 4/2000 | Thal | 6,562,071 | B2 | 5/2003 | Järvinen |
| 6,048,343 | A | 4/2000 | Mathis et al. | 6,565,572 | B2 | 5/2003 | Chappius |
| 6,053,916 | A | 4/2000 | Moore | 6,565,573 | B1 | 5/2003 | Ferrante et al. |
| 6,068,648 | A | 5/2000 | Cole et al. | 6,569,187 | B1 | 5/2003 | Bonutti et al. |
| 6,077,292 | A | 6/2000 | Bonutti | 6,572,655 | B1 | 6/2003 | Johnson |
| 6,096,060 | A | 8/2000 | Fitts et al. | 6,585,740 | B2 | 7/2003 | Schlapfer et al. |
| 6,117,160 | A | 9/2000 | Bonutti | 6,589,245 | B1 | 7/2003 | Weiler et al. |
| 6,117,162 | A | 9/2000 | Schmieding et al. | 6,607,548 | B2 | 8/2003 | Pohjonen et al. |
| 6,123,710 | A | 9/2000 | Pinczewski et al. | 6,620,166 | B1 | 9/2003 | Wenstrom, Jr. et al. |
| 6,143,017 | A | 11/2000 | Thal | 6,620,195 | B2 | 9/2003 | Goble et al. |
| 6,149,653 | A | 11/2000 | Deslauriers | 6,620,349 | B1 | 9/2003 | Lopez |
| 6,149,669 | A | 11/2000 | Li | 6,623,492 | B1 | 9/2003 | Berube et al. |
| 6,156,039 | A | 12/2000 | Thal | 6,623,524 | B2 | 9/2003 | Schmieding |
| 6,156,056 | A | 12/2000 | Kearns et al. | 6,629,977 | B1 | 10/2003 | Wolf |
| 6,159,234 | A | 12/2000 | Bonutti et al. | 6,635,073 | B2 | 10/2003 | Bonutti |
| 6,190,401 | B1 | 2/2001 | Green et al. | 6,652,562 | B2 | 11/2003 | Collier et al. |
| 6,190,411 | B1 | 2/2001 | Lo | 6,656,182 | B1 | 12/2003 | Hayhurst |
| 6,200,330 | B1 | 3/2001 | Benderev et al. | 6,663,634 | B2 | 12/2003 | Ahrens et al. |
| 6,206,883 | B1 | 3/2001 | Tunc | 6,663,656 | B2 | 12/2003 | Schmieding et al. |
| 6,210,376 | B1 | 4/2001 | Grayson | 6,666,868 | B2 | 12/2003 | Fallin |
| 6,214,012 | B1 | 4/2001 | Karpman et al. | 6,689,137 | B2 | 2/2004 | Reed |
| 6,228,096 | B1 | 5/2001 | Marchand | 6,712,849 | B2 | 3/2004 | Re et al. |
| 6,231,592 | B1 | 5/2001 | Bonutti et al. | 6,716,957 | B2 | 4/2004 | Tunc |
| 6,235,057 | B1 | 5/2001 | Roger et al. | 6,726,722 | B2 | 4/2004 | Walkenhorst et al. |
| 6,241,771 | B1 | 6/2001 | Gresser et al. | 6,746,483 | B1 | 6/2004 | Bojarski et al. |
| 6,245,081 | B1 | 6/2001 | Bowman et al. | 6,755,836 | B1 | 6/2004 | Lewis |
| 6,258,091 | B1 | 7/2001 | Sevrain et al. | 6,802,862 | B1 | 10/2004 | Roger et al. |
| 6,269,716 | B1 | 8/2001 | Amis | 6,808,526 | B1 | 10/2004 | Magerl et al. |
| 6,270,518 | B1 | 8/2001 | Pedlick et al. | 6,814,741 | B2 | 11/2004 | Bowman et al. |
| 6,273,890 | B1 | 8/2001 | Frazier | 6,830,572 | B2 | 12/2004 | McDevitt et al. |
| 6,283,973 | B1 | 9/2001 | Hubbard et al. | 6,863,671 | B1 | 3/2005 | Strobel et al. |
| 6,287,325 | B1 | 9/2001 | Bonutti | 6,872,040 | B2 | 3/2005 | Deeg et al. |
| 6,293,961 | B2 | 9/2001 | Schwartz et al. | 6,875,216 | B2 | 4/2005 | Wolf |
| 6,299,615 | B1 | 10/2001 | Huebner | 6,921,402 | B2 | 7/2005 | Contiliano et al. |
| 6,302,888 | B1 | 10/2001 | Mellinger et al. | 6,972,027 | B2 | 12/2005 | Fallin et al. |
| 6,306,159 | B1 | 10/2001 | Schwartz et al. | 6,980,903 | B2 | 12/2005 | Daniels et al. |
| 6,312,448 | B1 | 11/2001 | Bonutti | 6,989,034 | B2 | 1/2006 | Hammer et al. |
| 6,319,271 | B1 | 11/2001 | Schwartz et al. | 2001/0051816 | A1 | 12/2001 | Enzerink et al. |
| 6,328,758 | B1 | 12/2001 | Tornier et al. | 2002/0019649 | A1 | 2/2002 | Sikora et al. |
| 6,342,060 | B1 | 1/2002 | Adams | 2002/0058966 | A1 | 5/2002 | Tormala et al. |
| 6,343,531 | B2 | 2/2002 | Amis | 2002/0123752 | A1 | 9/2002 | Schultheiss et al. |
| 6,368,322 | B1 | 4/2002 | Luks et al. | 2002/0169452 | A1 | 11/2002 | Tormala et al. |
| 6,368,326 | B1 | 4/2002 | Dakin et al. | 2002/0169478 | A1 | 11/2002 | Schwartz et al. |
| 6,379,361 | B1 | 4/2002 | Beck, Jr. et al. | 2003/0009235 | A1 | 1/2003 | Manrique et al. |
| 6,383,199 | B2 | 5/2002 | Carter et al. | 2003/0032961 | A1 | 2/2003 | Pelo et al. |
| 6,387,113 | B1 | 5/2002 | Hawkins et al. | 2003/0033021 | A1 | 2/2003 | Plouhar et al. |

| | | | | | | |
|---|---|---|---|---|---|---|
| 2003/0033022 | A1 | 2/2003 | Plouhar et al. | EP | 0651979 | 5/1995 |
| 2003/0036797 | A1 | 2/2003 | Malaviya et al. | EP | 0669110 | 8/1995 |
| 2003/0036801 | A1 | 2/2003 | Schwartz et al. | EP | 0686373 | 12/1995 |
| 2003/0078617 | A1 | 4/2003 | Schwartz et al. | EP | 0775473 | 5/1997 |
| 2003/0083662 | A1 | 5/2003 | Middleton | EP | 0 913 123 A1 | 5/1999 |
| 2003/0088251 | A1 | 5/2003 | Braun et al. | EP | 0913131 | 5/1999 |
| 2003/0105477 | A1 | 6/2003 | Schwartz et al. | EP | 99121052.7 | 10/1999 |
| 2003/0130694 | A1 | 7/2003 | Bojarski et al. | EP | 99121106 | 10/1999 |
| 2003/0135214 | A1 | 7/2003 | Fetto et al. | EP | 0995409 | 4/2000 |
| 2003/0152522 | A1 | 8/2003 | Miller et al. | EP | 1 013 229 A2 | 6/2000 |
| 2003/0167072 | A1 | 9/2003 | Oberlander | EP | 1093773 | 4/2001 |
| 2003/0225459 | A1 | 12/2003 | Hammer et al. | EP | 1093774 | 4/2001 |
| 2004/0002734 | A1 | 1/2004 | Fallin et al. | FR | 2622790 | 12/1989 |
| 2004/0006345 | A1 | 1/2004 | Vlahos et al. | FR | 2688689 | 9/1993 |
| 2004/0006346 | A1 | 1/2004 | Holmen et al. | FR | 2717070 | 9/1995 |
| 2004/0015172 | A1 | 1/2004 | Biedermann et al. | FR | 2723528 | 2/1996 |
| 2004/0024456 | A1 | 2/2004 | Brown, Jr. et al. | FR | 2744010 | 8/1997 |
| 2004/0087981 | A1 | 5/2004 | Berube et al. | FR | 2745999 | 9/1997 |
| 2004/0122431 | A1 | 6/2004 | Biedermann et al. | FR | 2770764 | 5/1999 |
| 2004/0138664 | A1 | 7/2004 | Bowman | GB | 2 083 751 | 3/1982 |
| 2004/0138704 | A1 | 7/2004 | Gambale et al. | GB | 2 118 474 | 11/1983 |
| 2004/0143344 | A1 | 7/2004 | Malaviya et al. | GB | 2312376 | 10/1997 |
| 2004/0153103 | A1 | 8/2004 | Schwartz et al. | JP | 5362911 | 5/1978 |
| 2004/0166169 | A1 | 8/2004 | Malaviya | JP | 5362912 | 5/1978 |
| 2004/0220574 | A1 | 11/2004 | Pelo et al. | JP | 5374942 | 6/1978 |
| 2004/0225292 | A1 | 11/2004 | Sasso et al. | JP | 5378230 | 6/1978 |
| 2004/0243139 | A1 | 12/2004 | Lewis et al. | JP | 54-166092 | 11/1979 |
| 2004/0267164 | A1 | 12/2004 | Rhodes et al. | JP | 54-166093 | 11/1979 |
| 2004/0267265 | A1 | 12/2004 | Kyle | JP | 54-176284 | 12/1979 |
| 2004/0267270 | A1 | 12/2004 | Jacobs et al. | JP | 54-178988 | 12/1979 |
| 2004/0267276 | A1 | 12/2004 | Camino et al. | JP | 62-159647 | 7/1987 |
| 2004/0267277 | A1 | 12/2004 | Zannis et al. | JP | 62-295657 | 12/1987 |
| 2004/0267304 | A1 | 12/2004 | Zannis et al. | JP | 5269160 | 10/1993 |
| 2005/0027307 | A1 | 2/2005 | Schwartz et al. | JP | 7-51292 | 2/1995 |
| 2005/0033363 | A1 | 2/2005 | Bojarski et al. | JP | 10-211213 | 8/1998 |
| 2005/0074495 | A1 | 4/2005 | Schwartz et al. | WO | WO 83/00615 | 3/1983 |
| 2005/0090828 | A1 | 4/2005 | Alford | WO | WO 86/03666 | 12/1985 |
| 2005/0125073 | A1 | 6/2005 | Orban et al. | WO | WO 87/01270 | 3/1987 |
| 2005/0137600 | A1 | 6/2005 | Jacobs et al. | WO | WO 89/10096 | 11/1989 |
| 2005/0149033 | A1 | 7/2005 | McGuire et al. | WO | WO 93/15694 | 8/1993 |
| 2005/0159812 | A1 | 7/2005 | Dinger, III et al. | WO | WO 95/02373 | 1/1995 |
| 2005/0165482 | A1 | 7/2005 | Goldhahn et al. | WO | WO 97/37603 | 10/1997 |
| 2006/0030948 | A1 | 2/2006 | Manrique et al. | WO | WO 98/22047 | 5/1998 |
| 2006/0100627 | A1 | 5/2006 | Stone et al. | WO | WO 98/22048 | 5/1998 |
| 2006/0167482 | A1 | 7/2006 | Swain et al. | WO | WO-9822048 | 5/1998 |
| 2006/0293709 | A1 | 12/2006 | Bojarski et al. | WO | WO 99/01084 | 7/1998 |
| 2007/0055255 | A1 | 3/2007 | Siegel | WO | WO 99/12480 | 9/1998 |
| 2007/0078435 | A1 | 4/2007 | Stone et al. | WO | WO-9901084 | 1/1999 |
| 2007/0083236 | A1 | 4/2007 | Sikora et al. | WO | WO 99/44544 | 9/1999 |
| | | | | WO | WO 00/40159 | 7/2000 |
| | | | | WO | WO 01/39671 A1 | 7/2001 |

FOREIGN PATENT DOCUMENTS

| | | |
|---|---|---|
| AU | 4402/66 | 10/1967 |
| AU | 22237/67 | 11/1968 |
| AU | 50285/69 | 8/1970 |
| AU | 58504/69 | 1/1971 |
| AU | 59638/69 | 2/1971 |
| AU | 15054/70 | 11/1971 |
| AU | 36151/71 | 5/1973 |
| AU | 43812/68 | 9/1973 |
| AU | A-71108/87 | 10/1987 |
| DE | 2919009 C2 | 11/1979 |
| DE | 3027138 | 12/1981 |
| DE | 3225620 A1 | 2/1983 |
| DE | 3136083 | 3/1983 |
| DE | 233303 A1 | 2/1986 |
| DE | 4302397 | 7/1993 |
| DE | 29621340 | 5/1998 |
| DE | 19841252 | 3/2000 |
| EP | 0 108 912 A2 | 5/1984 |
| EP | 0 129 422 | 12/1984 |
| EP | 0 241 240 | 10/1987 |
| EP | 0 260 970 A2 | 3/1988 |
| EP | 0 315 371 A2 | 5/1989 |
| EP | 0 415 915 | 3/1991 |
| EP | 0440991 | 8/1991 |
| EP | 0441065 | 8/1991 |
| EP | 0 490 417 A1 | 6/1992 |
| EP | 0502698 | 9/1992 |
| EP | 0 598 219 A2 | 5/1994 |

| | | |
|---|---|---|
| WO | WO 02/36020 A1 | 10/2002 |
| WO | WO 03/071962 A2 | 9/2003 |
| WO | WO 03/077772 A1 | 9/2003 |
| WO | WO 2005/104992 | 11/2005 |

OTHER PUBLICATIONS

Arthrotek, A Biomet Company; Sure fire Hybrid Meniscal Device; Launch Date: Fall AANA 2004.

F. Alan Barber, M.D., "Uses and Abuses of Sutures and Anchors," Shoulder Scope, San Diego Shoulder Arthroscopy Library.

F. Alan Barber, M.D., "Using Sutures and Anchors," San Diego Shoulder Arthroscopy Course, 17th Annual Meeting.

Flavia Namie Azato, et al. "Traction endurance biomechanical study of metallic suture anchors at different insertion angles," Acta ortop. bras., vol. 11, No. 1, Sao Paulo, Jan./Mar. 2003.

Hecker At, et al., "Pull-out strength of suture anchors for rotator cuff and Bankart lesion repairs," Am J Sports Med. 1993.

Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.

Opus Medical; The AutoCuff System; www.opusmedical.com.; 2003.

Roy Alan Majors, M.D.; "Meniscal repairs: proven techniques and current trends," Lippincott Williams & Wilkins, Inc.; 2002.

Shoulder Arthroscopy; pp. H-2-H-22.

Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
A. Weiler, et al; Biodegradierbare Interferenzschrauben in der Kreuzbandchirurgie; OP-Journal 14 pp. 278-284; 1998.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
US 6,238,418, 05/2001, Schwartz et al. (withdrawn)

* cited by examiner

TISSUE FIXATION DEVICE

CROSS-REFERENCE TO RELATED APPLICATIONS

This application is a continuation-in-part of U.S. patent application Ser. No. 11/294,694 filed Dec. 5, 2005, which is a continuation-in-part of U.S. patent application Ser. No. 10/984,624 filed on Nov. 9, 2004. The disclosures of the above applications are incorporated herein by reference.

INTRODUCTION

Various methods of attaching tissue, such as soft tissue, grafts or ligaments to bone are known. In anterior or posterior cruciate ligament reconstruction (ACL or PCL), for example, interference screws can be used to secure the graft against the walls of tunnels drilled in the tibia and the femur. The interference screws are wedged between the graft and a wall of the tunnel. To facilitate insertion and improve anchoring, some interference screws include cutting threads or other anchoring features.

SUMMARY

The present teachings provide a method for securing a graft to a bone. The method includes forming a tunnel in the bone, positioning the graft in the tunnel, securing the graft in the tunnel with an anchor, and inserting biological material in a bore formed in the anchor.

The present teachings provide a method for securing a graft to a bone. The method includes forming a tunnel in the bone, positioning at least a portion of the graft in the tunnel, securing the graft in the tunnel with an anchor, shaping biological material into a plug that conforms to a shape of a bore formed in the anchor, and inserting the plug in the bore of the anchor.

The present teachings provide a method for securing a graft to a bone. The method includes forming a tunnel in the bone, positioning at least a portion of the graft in the tunnel, securing the graft in the tunnel with an anchor, shaping biological material into a plug that conforms to a shape of a bore formed in the anchor, and inserting the plug in the bore of the anchor.

Further areas of applicability of the present invention will become apparent from the detailed description provided hereinafter. It should be understood that the detailed description and specific examples, while indicating various aspects of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DESCRIPTION OF VARIOUS ASPECTS

The following description is merely exemplary in nature and is in no way intended to limit the invention, its application, or uses. For example, although the devices and methods of the invention are illustrated for use in anterior cruciate ligament reconstruction (ACL) in knee surgery, uses in posterior cruciate ligament reconstruction (PCL) in knee surgery, and uses for securing any soft tissue, hard tissue, bone cartilage, ligament,soft tissue, bone-tendon-bone, natural or artificial graft, such as, for example, polylactide (PLA), polyglolide (PGA), polyurethane urea, and other grafts, to a bone are contemplated.

Figure 1:
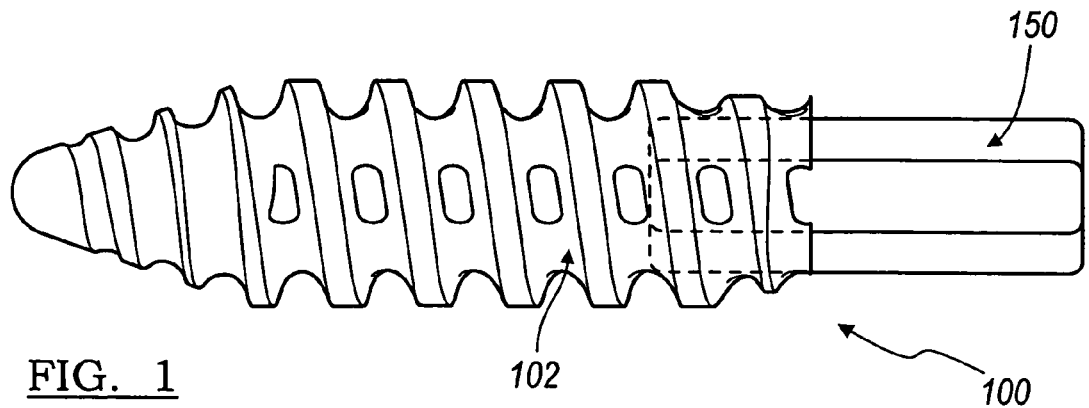
FIG. 1 is a partially assembled perspective view of a fixation device according to the present teachings.

Referring to FIG. 1, an exemplary fixation device 100 according to the present teachings includes a cannulated anchor 102 and a plug 150 that can be received in the anchor 102. FIGS. 2-5 illustrate exemplary anchors 102 and plugs 150. The cannulated anchor 102 includes a cylindrical portion 106 and a tapered tip portion 104. The anchor 102 can be threaded. The cylindrical portion 106 can have threads 114 with pitch $p_1$, and the tapered tip portion 104 can have threads 110 with a different pitch $p_2$. For an exemplary 30 mm long anchor, for example, $p_1$ can be about 2.2 mm and $p_2$ about 1.8 mm, or the other way around, or other values can be used for these dimensions. The threads 114, 110 of both portions 106, 104 can have "blunt" edges that are herein defined as non-cutting edges 108. The pitch $p_2$ of the tapered tip portion 104 can be selected, for example, to facilitate the insertion of the anchor 102 while using only non-cutting edges 108 and avoiding the need for sharp or cutting edges.

Figure 2:
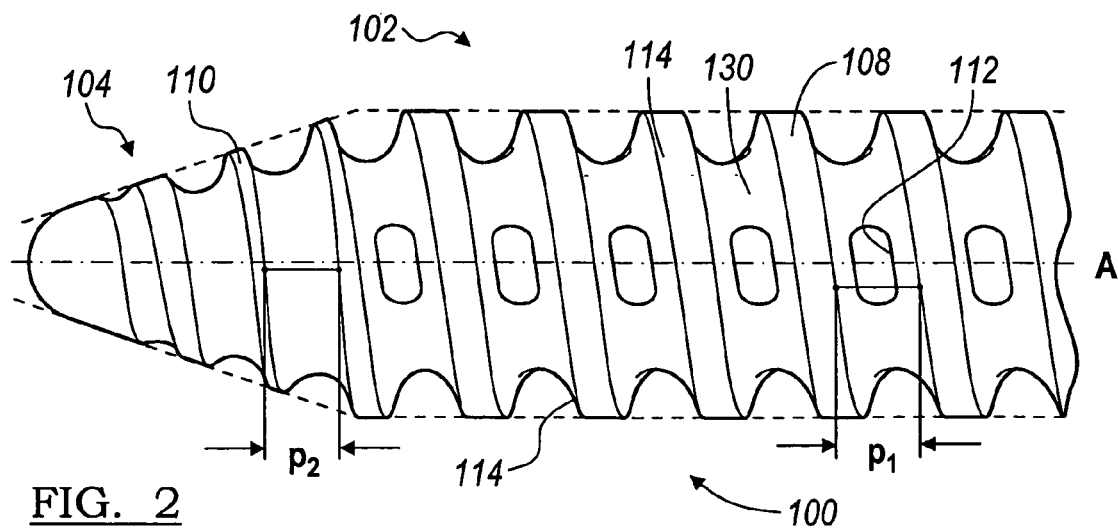
FIG. 2 is a perspective view of an anchor for a fixation device according to the present teachings.
Figure 2A:
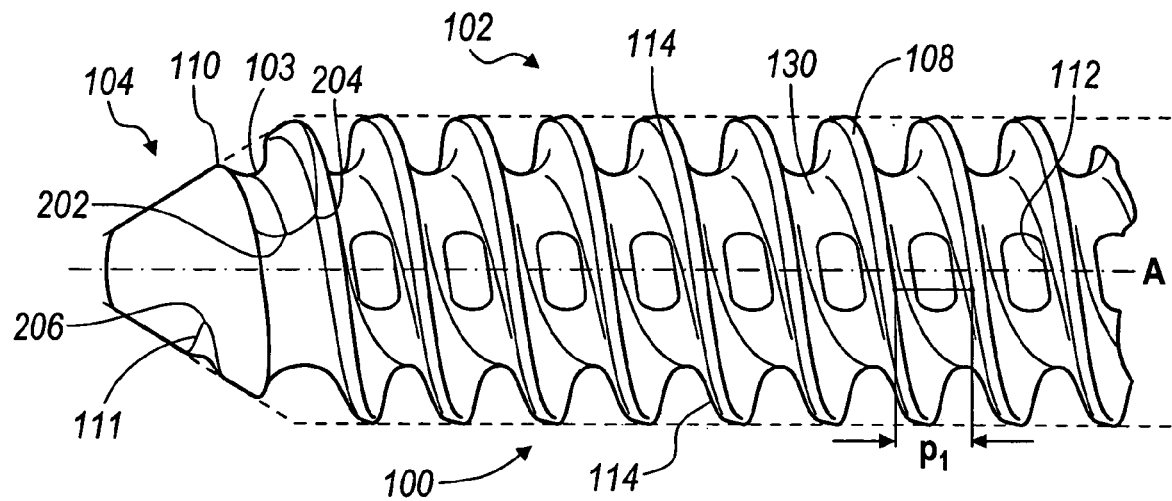
FIG. 2A is a perspective view of an anchor for a fixation device according to the present teachings.
Figure 2B:
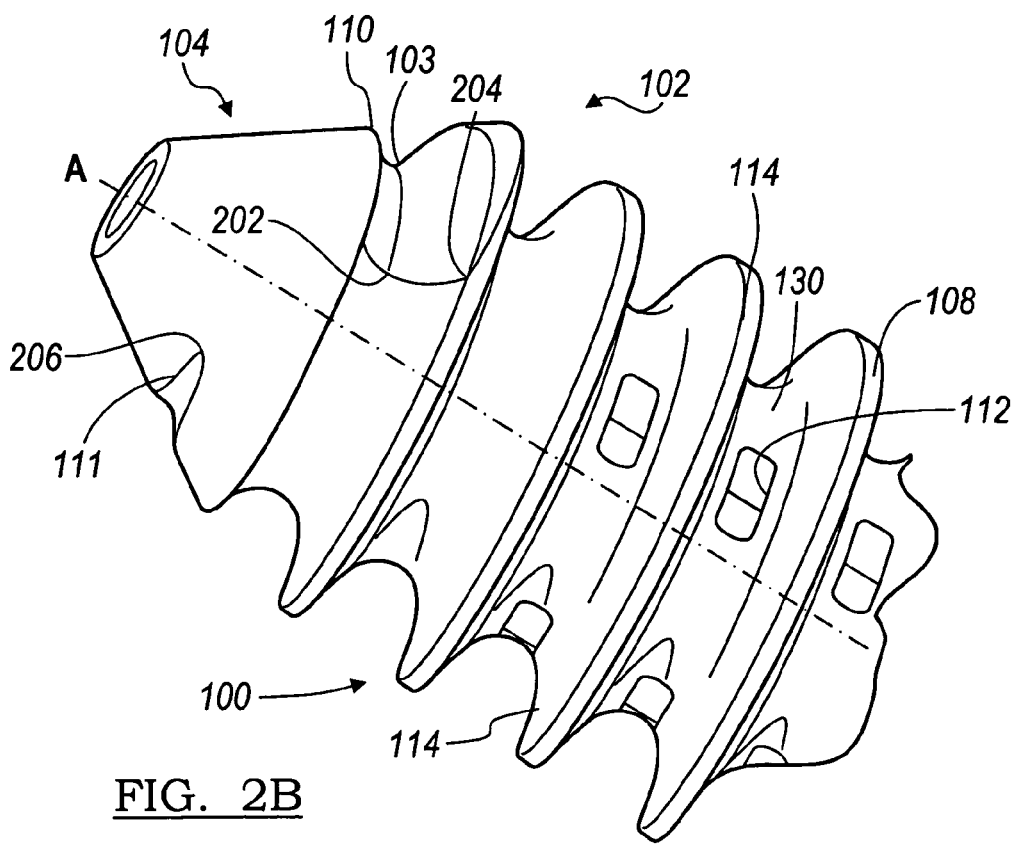
FIG. 2B is a perspective view of an anchor for a fixation device according to the present teachings.
Figure 2C:
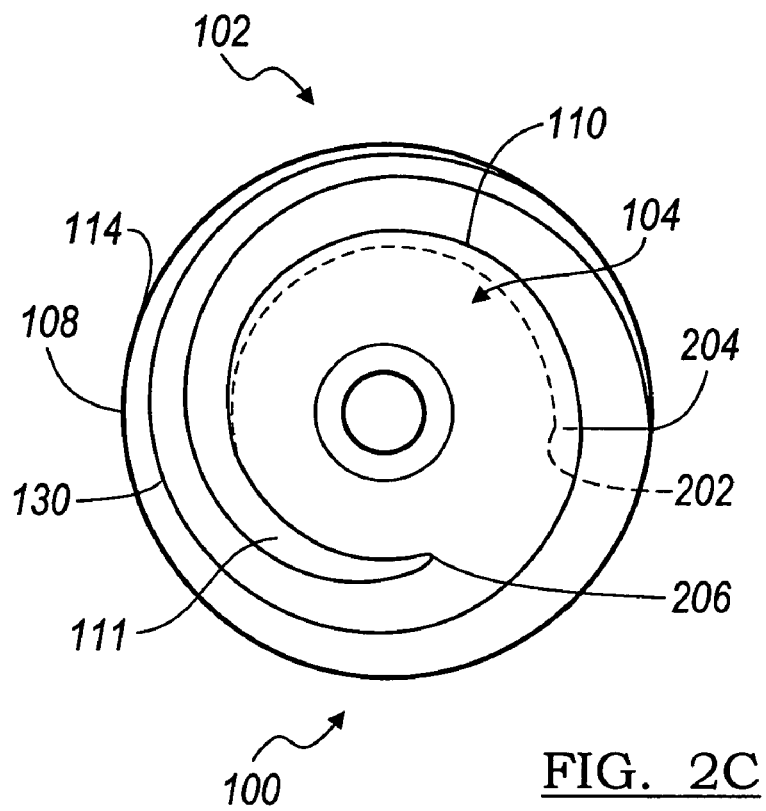
FIG. 2C is an end view of the anchor of FIG. 2B.

Referring to FIGS. 2A, 2B and 2C, the tapered tip portion 104 can include a partial/incomplete winding 111 (i.e. less than one winding) that extends less than one complete turn or winding (less than 360 degrees) around the tapered tip 104. The incomplete winding 111 can start, for example, at location 206 and terminate at locations 202, 204 having a rotation of about 300-degrees from the starting location 206. In this manner, the incomplete winding 111 reaches both the maximum diameter of the thread 110 and the maximum diameter of the root 103 of the thread 110 in less than one winding or about 300-degrees in the tapered tip portion 104. The incomplete winding 111 in synergy with the non-cutting edges 108 throughout the threads 114, 110 can further facilitate a gradual and controlled insertion of the anchor 102, thereby reducing damage to surrounding tissue. The incomplete winding 111 is also illustrated in FIGS. 3B and 3C, discussed below.

Figure 8:
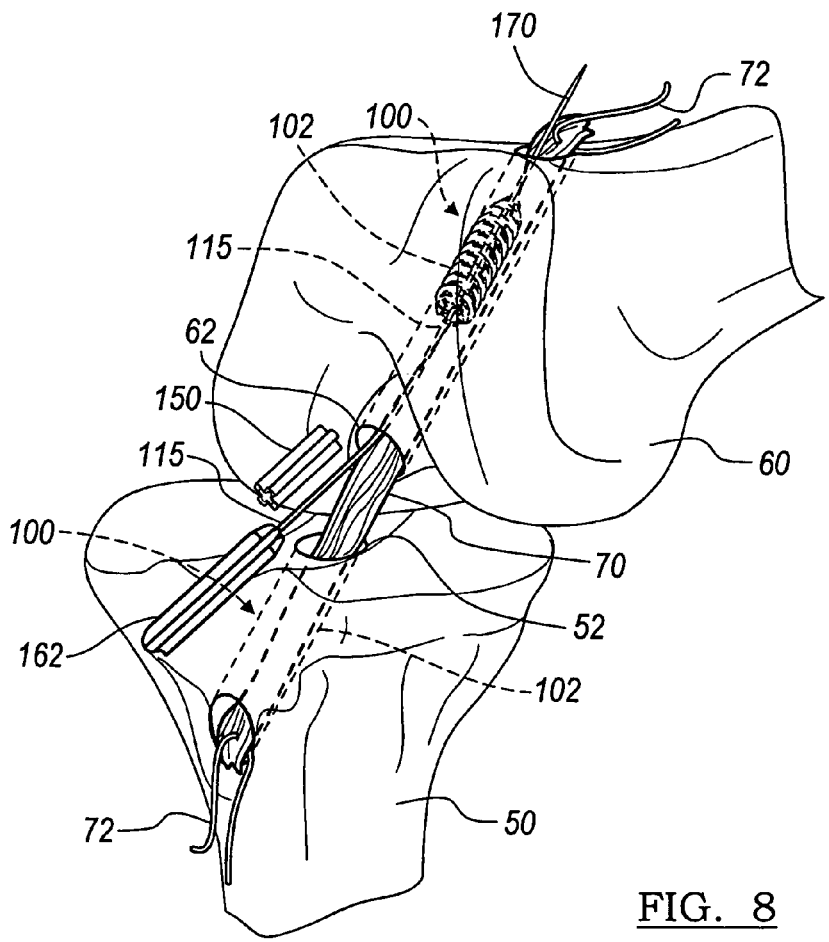
FIG. 8 is an environmental view of a fixation device according to the present teachings.

Referring to FIG. 8, the shape of the tapered tip portion 104 together with the smaller pitch threads 110 or partial thread 111 facilitates the insertion of the anchor 102 into a bone tunnel 62 to wedge a ligament or graft 70 against the wall of the tunnel 62 by pushing apart, without cutting into, surrounding tissues, including both bone and soft tissue graft. The threads 114 of the cylindrical portion 106 can also push apart, without cutting into, surrounding tissue, and do not follow any paths that may be opened by the pushing apart action of the threads 110 of the tapered tip portion 104. The anchor 102 can be made of any biocompatible material, including metal, such as titanium, for example. The anchor 102 can also be made of bioabsorbable/resorbable material, such as Lactosorb® from Biomet, Inc., Warsaw, Ind., for example.

Figure 3:
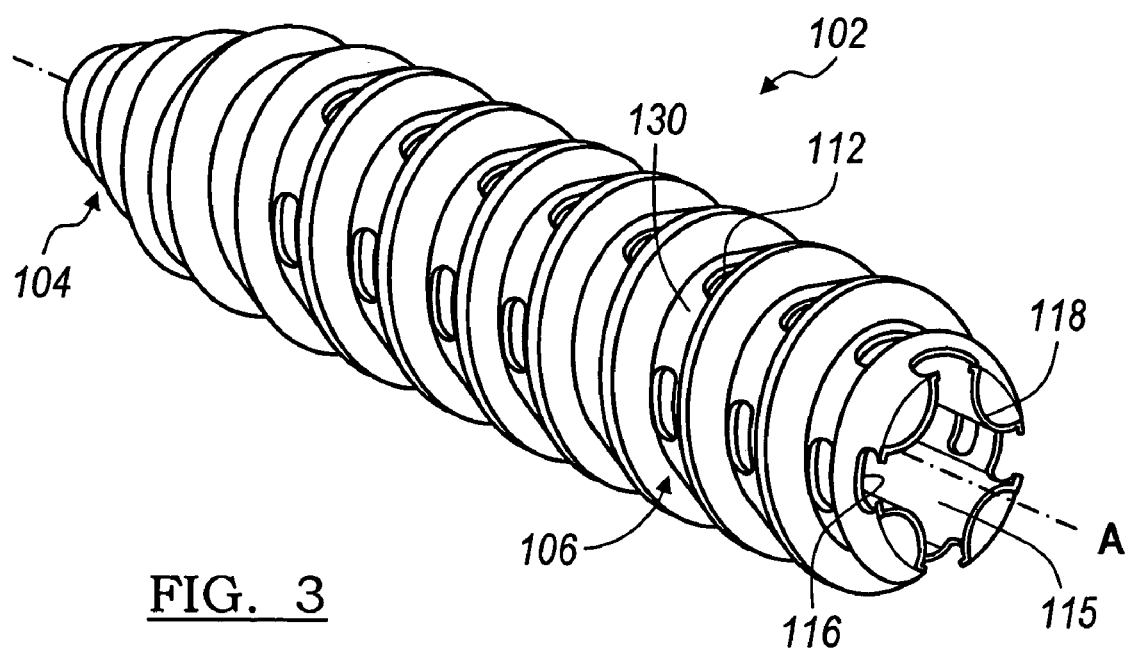
FIG. 3 is a perspective view of an anchor for a fixation device according to the present teachings.
Figure 3A:
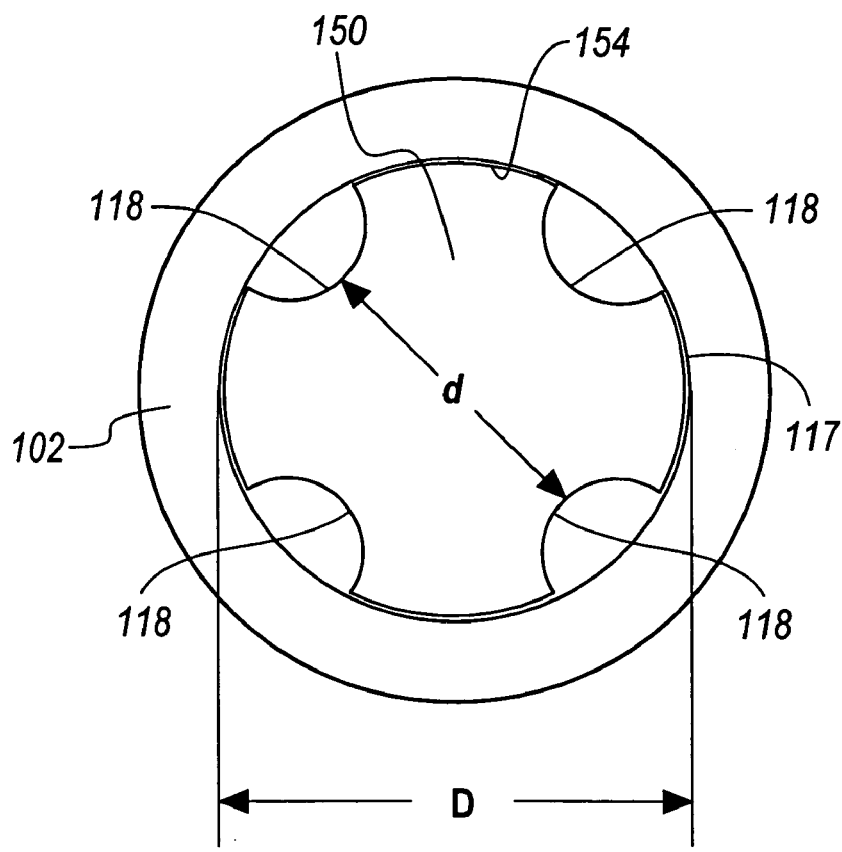
FIG. 3A is a cross-sectional view of a cannulated anchor with a plug inserted therein for a fixation device according to the present teachings.
Figure 3B:
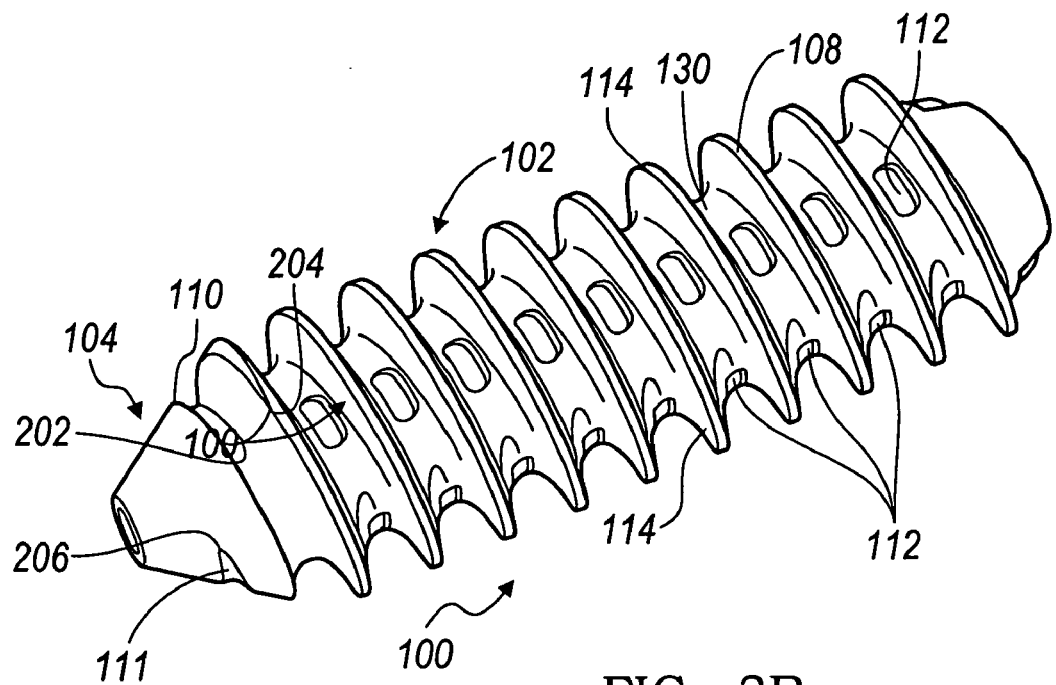
FIG. 3B is a perspective view of an anchor for a fixation device according to the present teachings.
Figure 3C:
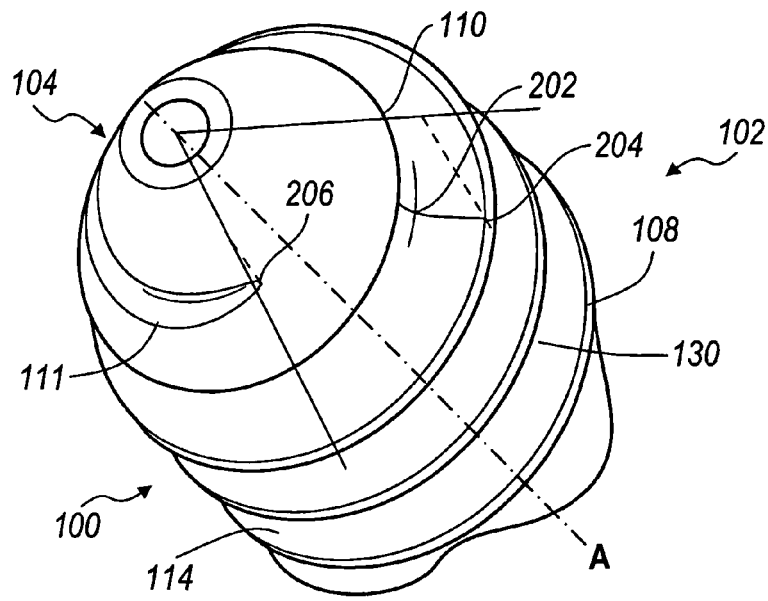
FIG. 3C is a perspective view of an anchor for a fixation device according to the present teachings.
Figure 3D:
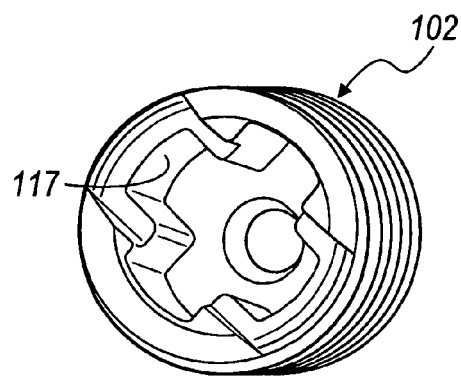
FIG. 3D is a perspective view of an anchor for a fixation device according to the present teachings.
Figure 3E:
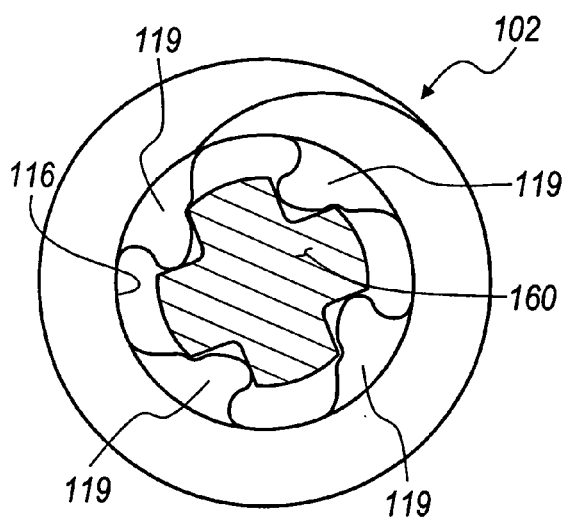
FIG. 3E is an end view of an anchor for a fixation device according to the present teachings shown coupled with an insertion driver.
Figure 3F:
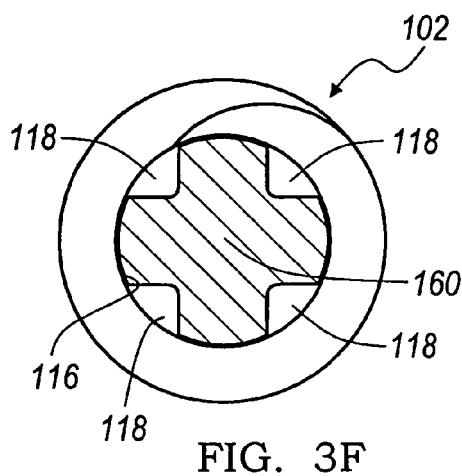
FIG. 3F is an end view of an anchor for a fixation device according to the present teachings shown coupled with an insertion driver.

Referring to FIGS. 3, 3A-F, 5 and 6, the cannulated body of the anchor 102 defines a longitudinal passage 115 that extends throughout the entire body of the anchor 102 along a longitudinal center axis "A". A plug-receiving portion or bore 116 of the longitudinal passage 115 can extend along the cylindrical portion 106 of the anchor and can have an enlarged opening of a shape, such as a cruciate shape defined by four longitudinal ribs 118, or any other shape, such as a fingered -shape, a hexagonal, pentagonal, triangular or other polygonal or curvilinear shape. In one aspect, the plug-receiving portion 116 can include asymmetric lobes 119 defining an asymmetric opening for the passage 115, such that the same size insertion tool or driver 160 can be used for different size anchors 102, as illustrated in FIGS. 3E and 3F. For example, the driver 160 can substantially occupy the cruciate cross-section of the plug-receiving portion 116 of the anchor 102 and conform substantially with the entire profile of the ribs 118, as illustrated in FIG. 3F. The same driver 160 can be used with a larger anchor 102, as illustrated in FIG. 3E, such that the driver 160 can be captured by the end portions of the asymmetric lobes 119 without substantially occupying the entire cross-section of the plug-receiving portion 116.

The plug 150 can have a shape that is complementary to the shape of the plug-receiving portion 116. For example, for the cruciate shape the plug 150 can have grooves 152 shaped for mating with the ribs 118 (or lobes 119) when the plug 150 is inserted into the passage 115. The plug 150 can be made of osteoinductive and/or osteoconductive material to promote bone growth through the anchor 102. The material of the plug 150 can be, for example, calcium phosphate, calcium sulfate, tricalcium phosphate, allograft bone, autograft bone, demineralized bone matrix, coral material, combinations thereof, etc. The plug can also be made from ProOsteon, available from Interpore Cross International, Irvine, Calif. The plug 150 can also be cannulated for engaging an insertion tool, and/or for facilitating tissue growth and/or injecting biologic agents therethrough.

Referring to FIGS. 2 and 3, the outer surface 130 of the cylindrical portion 106 of the anchor 102 between the threads 114 can include apertures 112. The apertures 112 can be formed, for example, by cutting through, from the inside to the outside, the outer surface 130 of the anchor 102 between the threads 114, using a cutting instrument that can be received in the anchor 102, although other cutting methods can also be used. The apertures 112 can also be formed not by cutting, but by using an appropriate insert/plug during the molding process of the anchor 102. The apertures 112 can, therefore, be arranged along the direction of the longitudinal axis A between adjacent threads 114 of the cylindrical portion 106. The apertures 112 can extend substantially between the threads 114 and ribs 118, occupying the entire wall-less region therebetween. The size of the apertures 112 can be selected to occupy only a portion of the outer surface 130 between the threads 114 and the ribs, as illustrated in FIG. 2.

Referring to FIG. 3, in one aspect, the size of the apertures 112 can be selected to occupy the entire portion of the outer surface 130 between the threads 114 and the ribs 118. In this respect, the structural integrity of the cylindrical portion 106 of the anchor 102 can be provided by the threads 114 and the ribs 118, which together form an open structural framework with no material wall therebetween. In this manner, the anchor 102 is molded as a rib/thread framework that does not include any wall structures therebetween, the apertures 112 defined by the absence of such wall material. The apertures 112 can facilitate bone ingrowth or outgrowth through the anchor 102 and can also be used to distribute a biologic material, including osteoinductive/osteoconductive material, such as calcium phosphate, platelet concentrates, fibrin, etc., which may be injected through the passage 115. The plug 150, in addition to providing bone growth promoting benefits, closes the longitudinal passage 115 and can substantially prevent such material from draining out through the apertures 112.

Referring to FIG. 3A, the outer surface 154 of the plug 150 can be shaped to extend outward beyond a minor diameter "d" defined by the ribs 118. The outer surface 154 of the plug can mate with an interior surface 117 of the anchor 102 at a major diameter "D" of the interior surface 117 at which the apertures 112 are formed, such that portions of the plug 150 can contact tissue through the apertures 112 when the anchor 102 is implanted, thereby promoting tissue growth and better tissue attachment.

Referring to FIGS. 4, 4A-4E, and 5, the cylindrical portion 106 of the anchor can also be solid, without any apertures. In particular, the cylindrical portion 106 can be formed to include a plurality of thin-walled window covers 113, which, because of their reduced dimensions, can quickly be resorbed after implantation of the anchor 102. Accordingly, the window covers 113 are resorbed at a different rate and preferentially relative to other portions of the cylindrical portion 106, thereby defining a plurality of apertures 112, similar to the apertures 112 described above in connection with FIGS. 2 and 3, and providing similar growth promoting properties. Including the window covers 113 in the anchor 102 can simplify the manufacturing process for the anchor 102. For example, any special precautions for keeping the plurality of apertures 112 open during molding are no longer necessary when window covers 113 provided. The presence of window covers 113 during the insertion of the anchor 102 can facilitate the insertion of the anchor 102 by reducing friction and the associated insertion torque. Similarly to the apertures 112, the window covers 113 can extend between adjacent threads 114 of the cylindrical portion 106, substantially parallel to the threads 114 in the regions between adjacent ribs 118. After resorption, the window covers 113 define apertures substantially similar to the pre-formed apertures 112 of the anchors 102 illustrated in FIG. 1, 2 or 3.

Figure 7A:
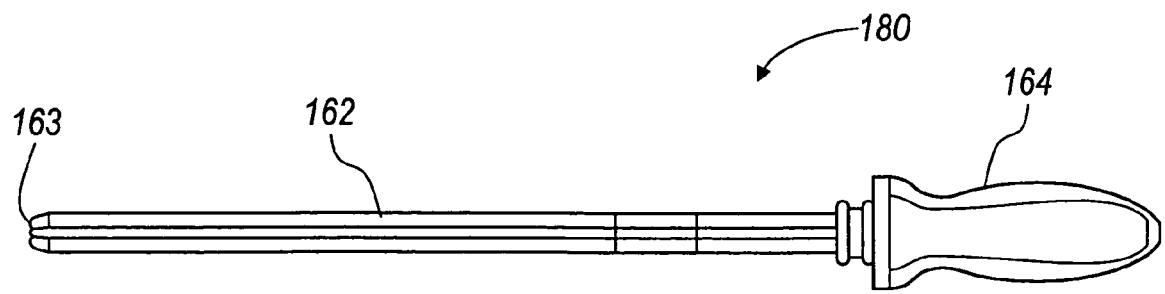
FIG. 7A is a perspective view of a driver for use with a fixation device according to the present teachings.

Referring to FIG. 7A, an exemplary driver 180 that can be used to rotate the anchor 102 and facilitate its insertion is illustrated. The driver 180 can include a handle 164 and a suitably shaped shaft 162 for engaging the plug-receiving portion 116 of the passage 115 of the anchor 102. The handle 164 can be modularly connected to the shaft 162. Alternatively, the plug 150 can be pre-inserted into the anchor 102 and the driver 180 can engage the cannulated plug 150. The driver 180 can also be cannulated. The shaft 162 can have a cruciate shape or any other shape that can engage the plug-receiving portion 116 and can terminate at a tapered end 163.

Figure 7B:
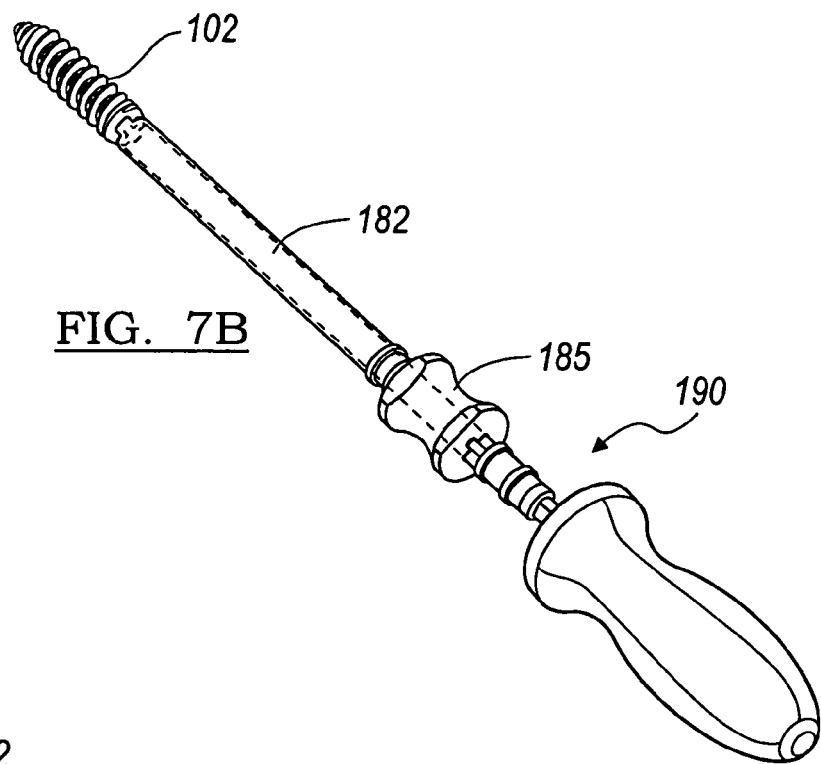
FIG. 7B is a perspective view of an inserter assembly shown coupled with a fixation device according to the present teachings.
Figure 7C:
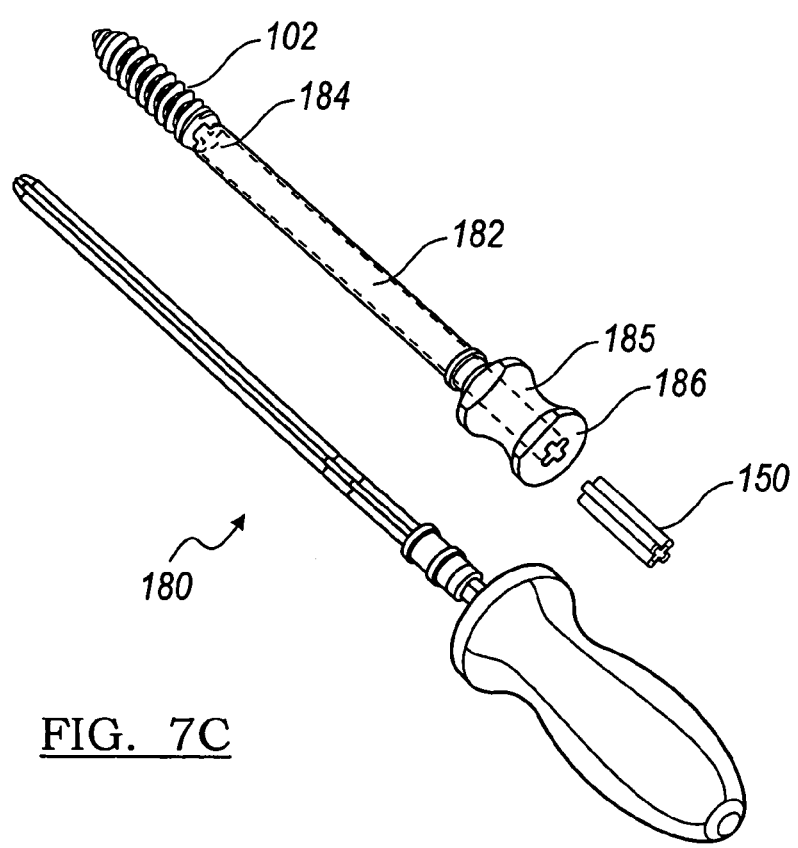
FIG. 7C is an exploded view of an inserter assembly shown with a fixation device according to the present teachings.
Figure 7D:
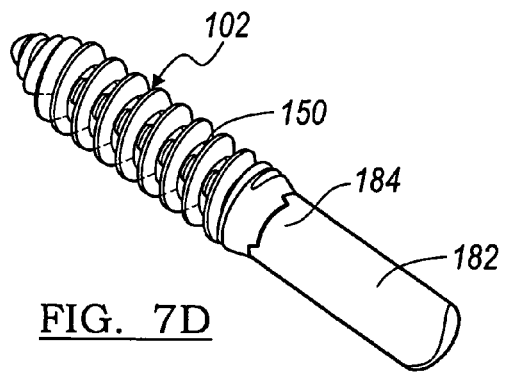
FIG. 7D is a perspective view of the fixation device of FIG. 7C shown with a sleeve of the inserter assembly attached thereon.
Figure 7E:
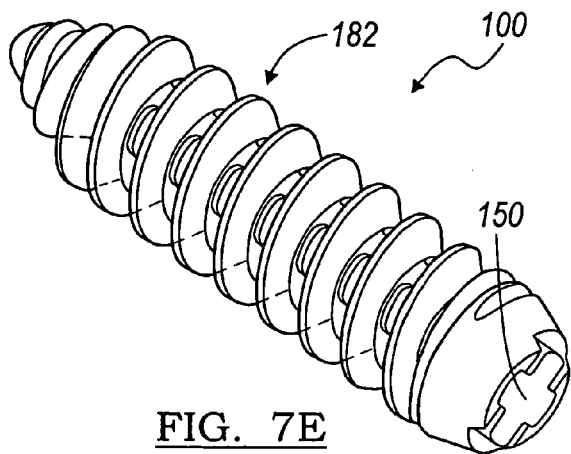
FIG. 7E is a perspective view of the fixation device of FIG. 7D shown after the inserter assembly is removed.

Referring to FIGS. 7A-7C, and FIG. 8A, an inserter assembly 190 for facilitating the insertion of the anchor 102 and plug 150 is illustrated. The inserter assembly 190 can include the driver 180 described above, and an anchor sleeve 182. The driver 180 can be used to apply torque to the interior surface 117 of the anchor 102 to insert the anchor 102 into the implantation site. The driver 180 can slide through the anchor sleeve 182 and the bore 116 of the anchor 102 to engage the anchor 102, as illustrated in FIG. 7B. The anchor sleeve 182 can have a distal end 184, which can be two-pronged or otherwise configured to mate or engage proximally of the anchor 102, and a tubular element 185 modularly or integrally coupled to the proximal end 186 of the sleeve 182. After the anchor 102 is inserted in the desired location, the driver 180 can be removed from the anchor sleeve 182, and the anchor sleeve 182 can remain engaged with the anchor 102, as illustrated in FIG. 7C. The plug 150 can be inserted from the proximal end 186 of the anchor sleeve 182. The driver 180 can be re-inserted into the proximal end 186 of the anchor sleeve 182 through the tubular element 185. A pusher, plunger or other driver tool can be used for forcing the plug 150 through the anchor sleeve 182 and into the plug-receiving portion 116 of the anchor 102, as illustrated in FIG. 7C. The plug 150 can be secured by interference fit into the anchor 102. After the plug 150 is fully seated within the anchor 102, as illustrated in FIG. 7D, the anchor sleeve 182 can be disengaged from the anchor 102 by axial pulling, and completely removed, as illustrated in FIG. 7E.

Referring to FIG. 8, an exemplary, but not limiting, use of the fixation device 100 is illustrated in the context of arthroscopic knee surgery. A ligament or graft 70 passes through a tibial tunnel 52 and a femoral tunnel 62 and is fixed in the tibia 50 and femur 60 with sutures 72. The fixation device 100 can be implanted in the tibial tunnel 52 or in the femoral tunnel 62, or two fixation devices 100 can be implanted, one in each tunnel 52, 62. A nitinol or other guide wire 170 can be inserted between the wall of tibial tunnel 52 and/or femoral tunnel 62 and the graft 70 to guide the anchor 102 of the fixation device 100, as needed. The anchor 102 can be passed over the guide wire 170 and wedged between the graft 70 and the tibial tunnel 52 and/or femoral tunnel 62 by rotation using the cannulated driver 160. The guide wire 170 can then be removed. The passage 115 can be closed by inserting the plug 150. The inserter assembly 190 can be used for inserting the anchor 102 and the plug 150, as described in connection with FIGS. 7A-E above.

Figure 8A:
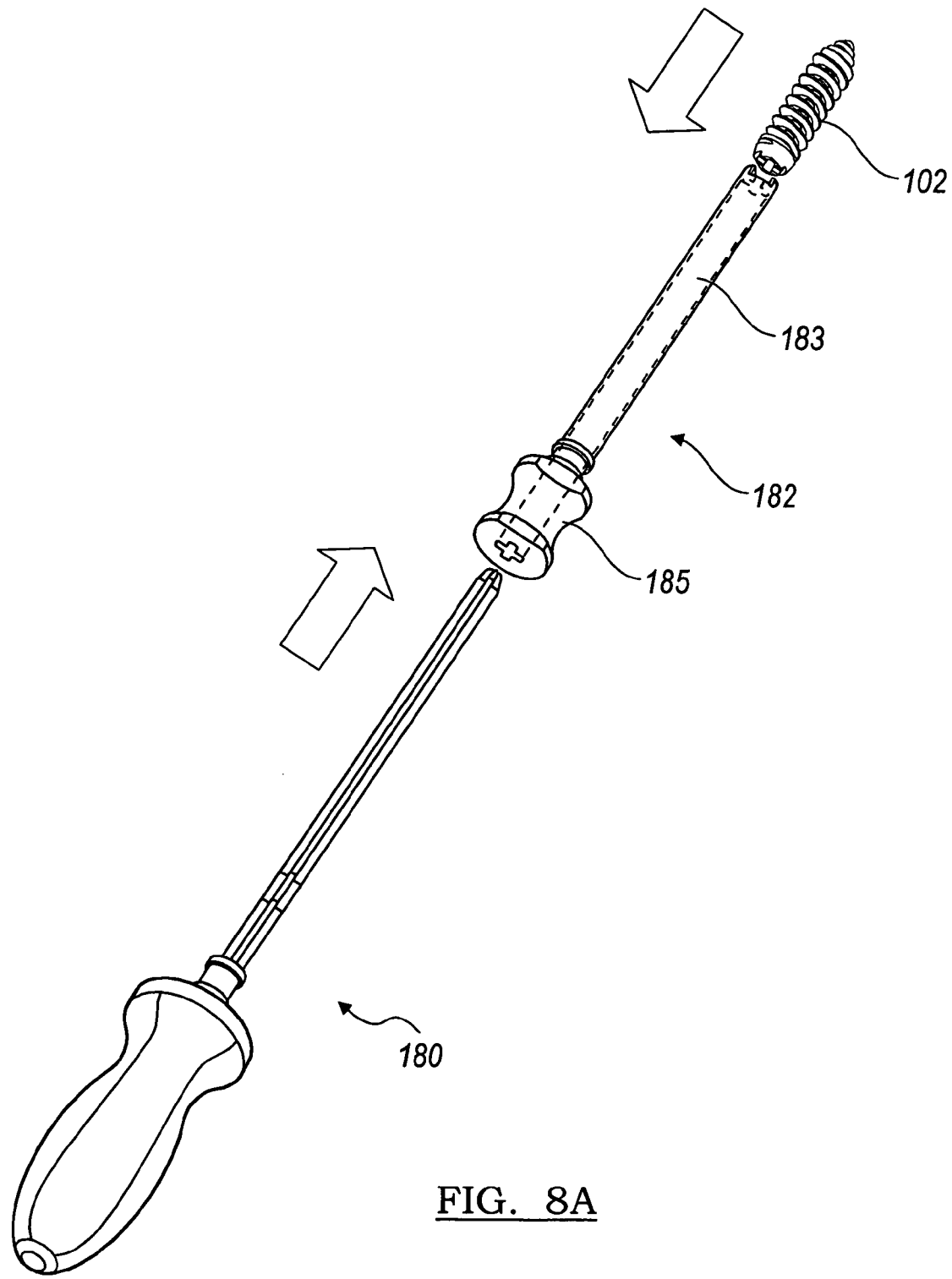
FIGS. 8A through 8G illustrate aspects of implanting a fixation device according to the present teachings.
Figure 8B:
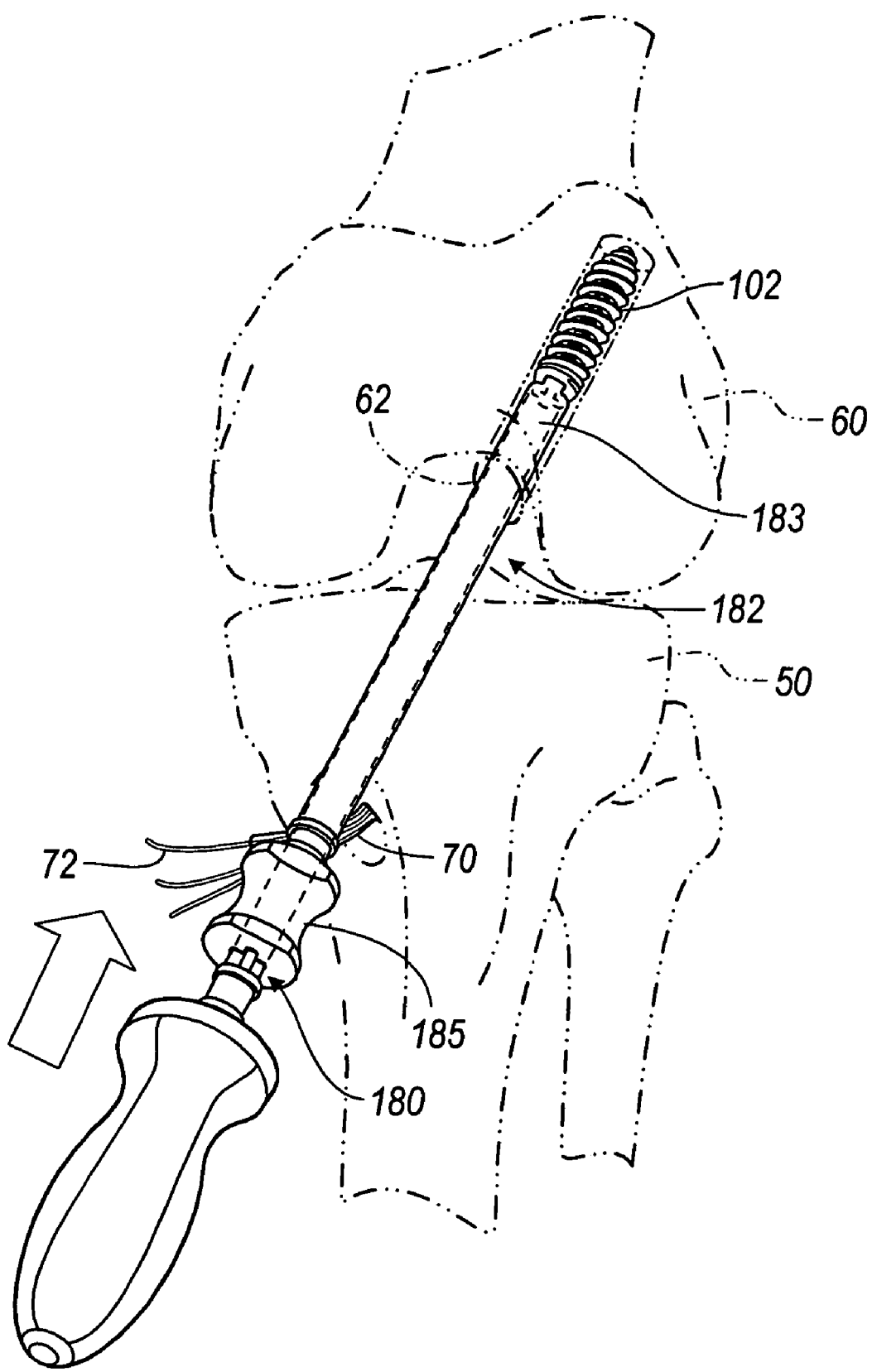
Figure 8C:
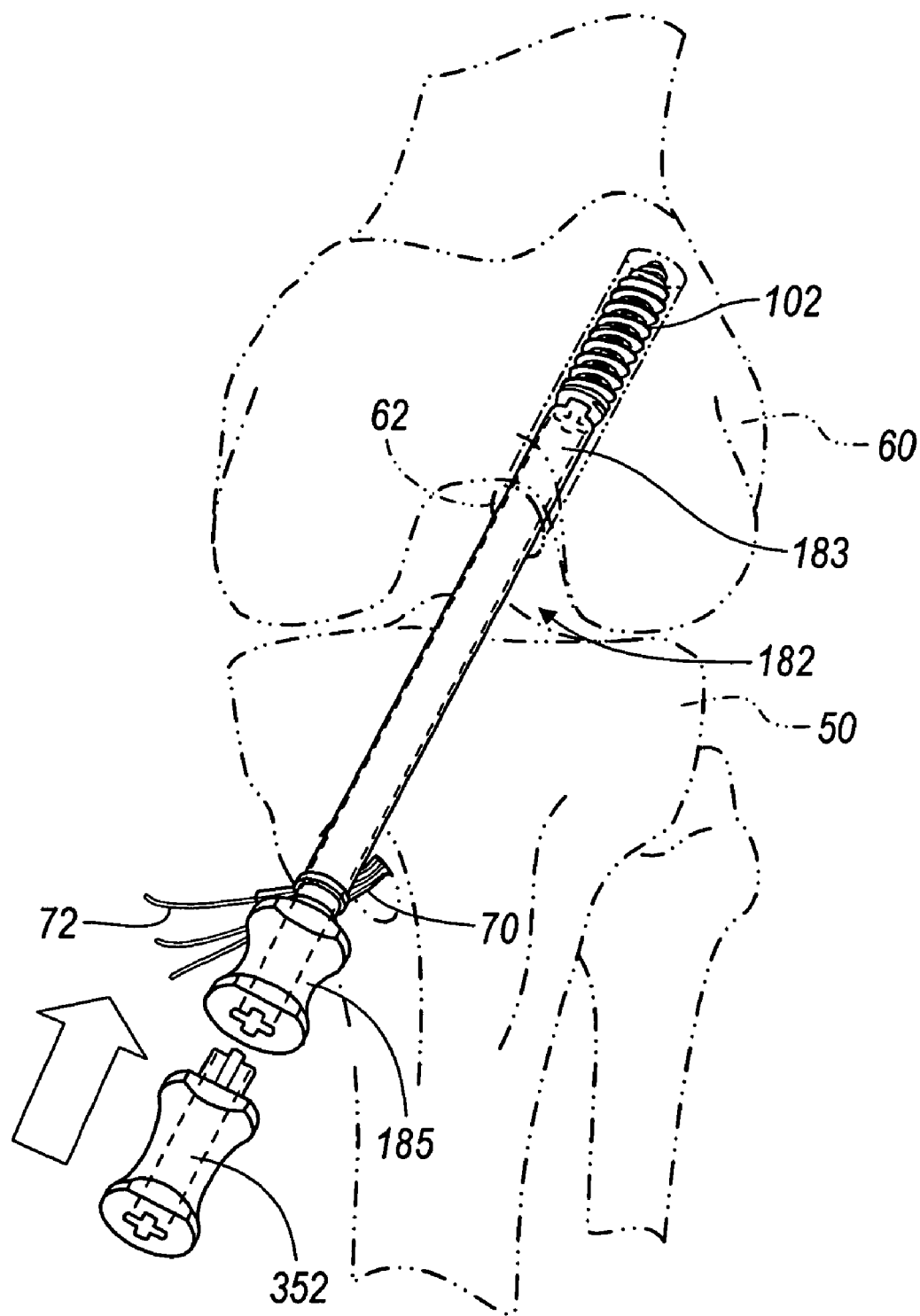
Figure 8D:
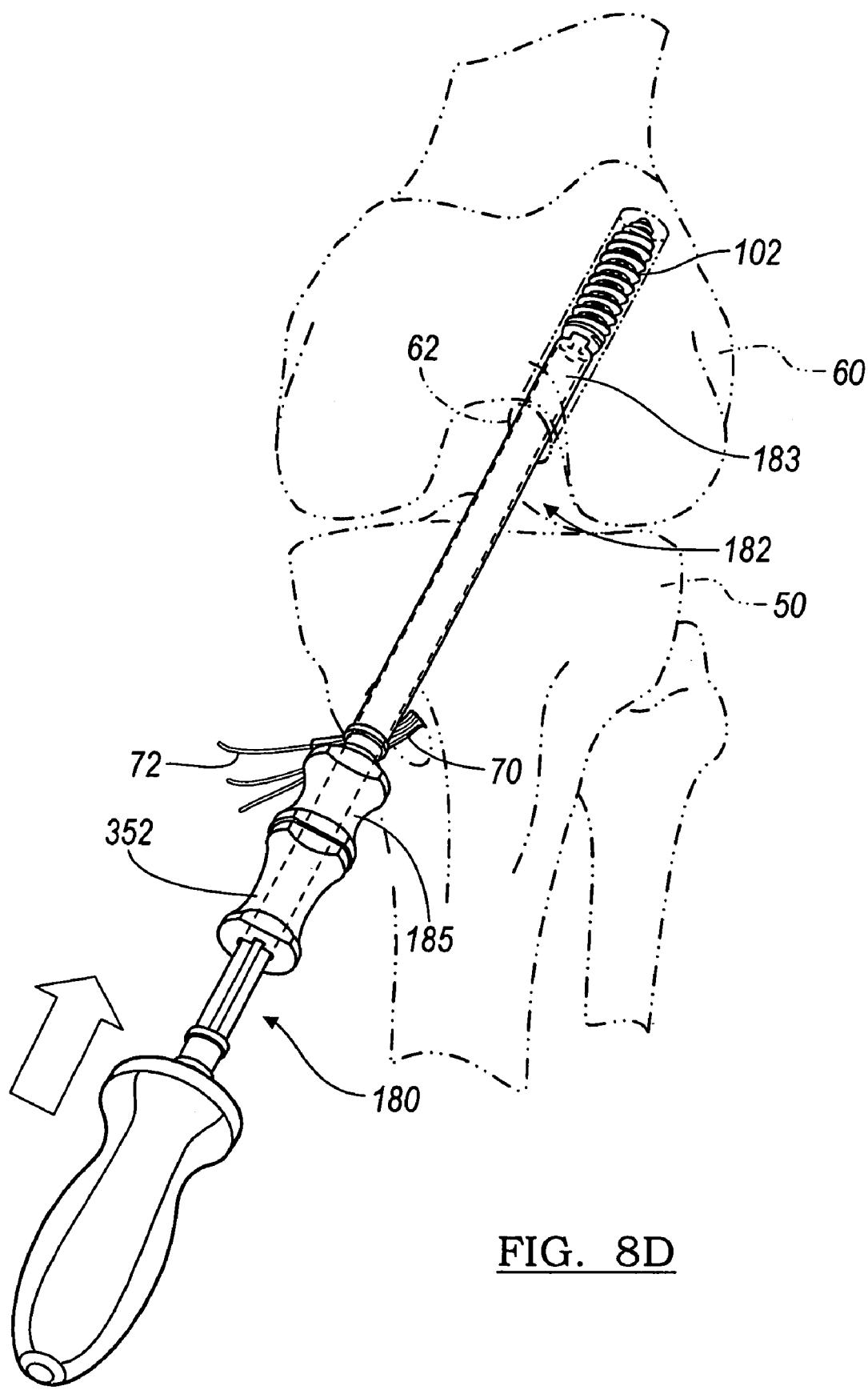
Figure 8E:
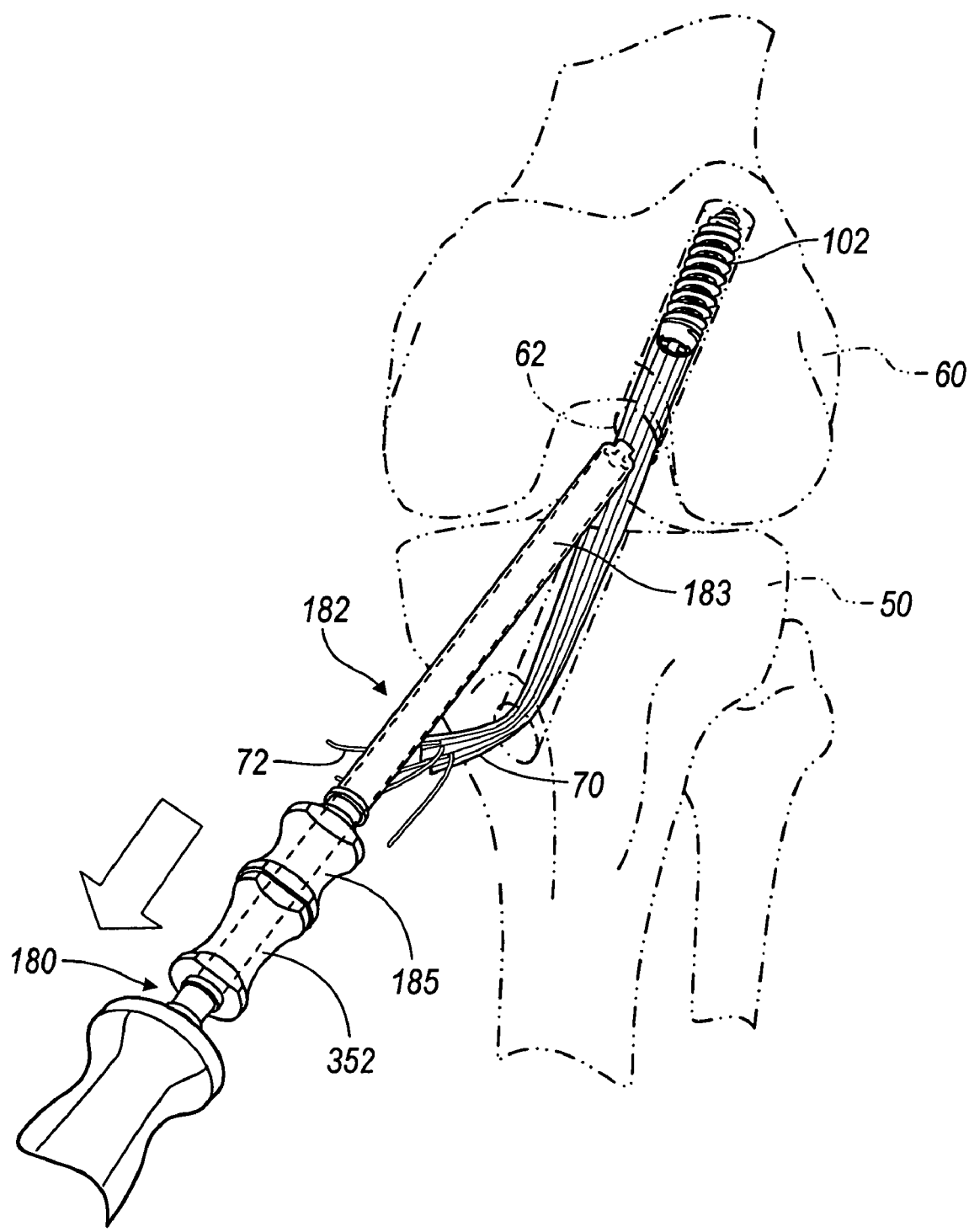
Figure 8F:
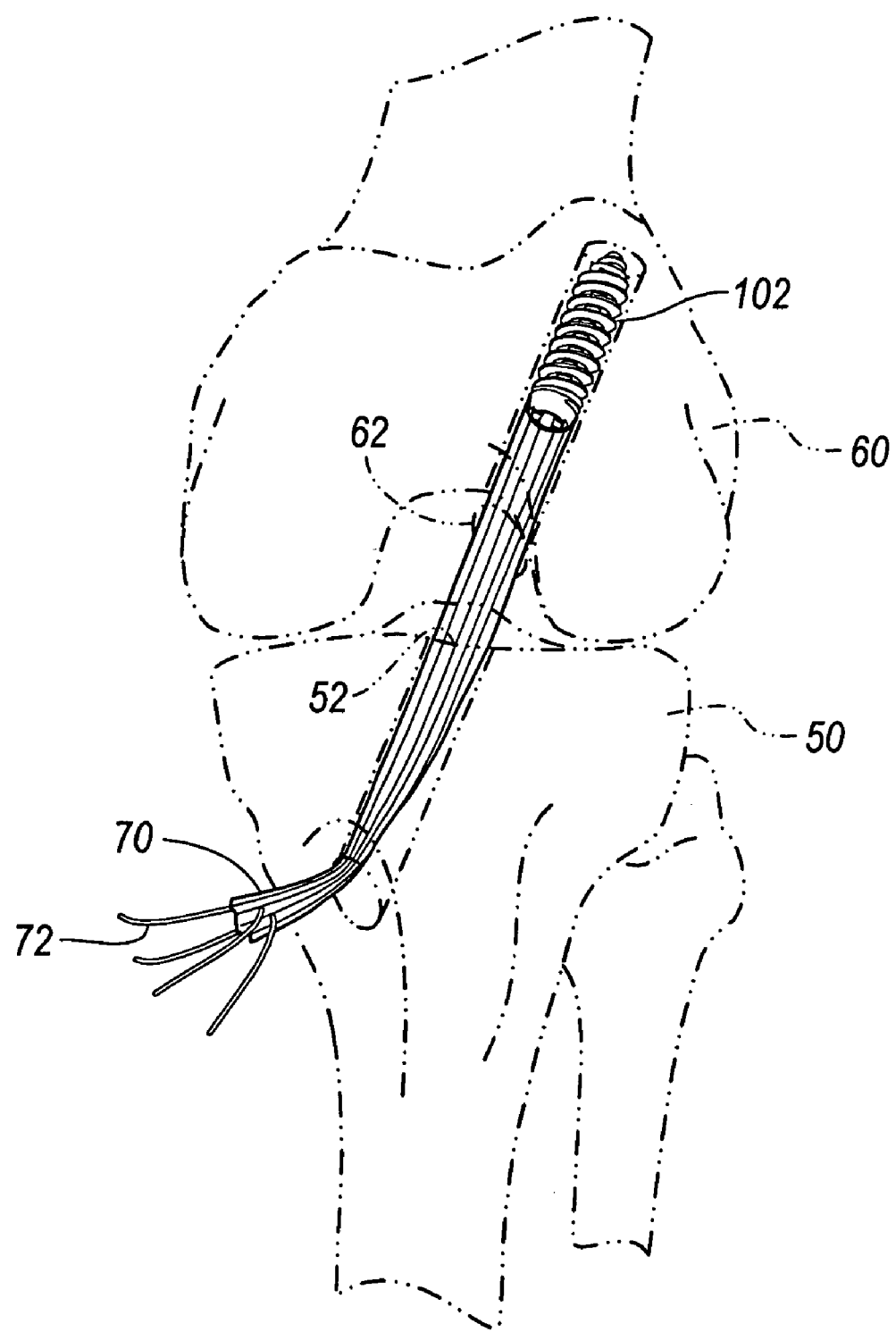

Referring to FIGS. 8A-8F, a single anchor 102 can be inserted in the femoral tunnel 62, after the graft 70 has been seated. Referring to FIG. 8A, the driver 180 can be slidably inserted through the sleeve 182 into the anchor 102 for engaging the anchor 102 as described above. The driver 180 with the sleeve 182, can be used to implant the anchor 102 into the femoral tunnel 62, as illustrated in FIG. 8B. The driver 180 can then be removed, and a compactor or plug sleeve 352 similar to the tubular element 185 of the anchor sleeve 182, can be coupled to the anchor sleeve 182, as illustrated in FIG. 8C. The plug sleeve 352 can be cannulated for matingly receiving the plug 150. The plug 150 or other biological material can be inserted through the plug sleeve 352 and pushed into the passage 115 of the anchor 102 using the driver 180 or other pusher tool, as illustrated in FIG. 8D. The driver 180 and the sleeve 182 can be disengaged from the anchor 102 and removed, as illustrated in FIG. 8E, leaving the anchor 102 in the femoral tunnel 62 engaging the graft 70, as illustrated in FIG. 8F.

Figure 8G:
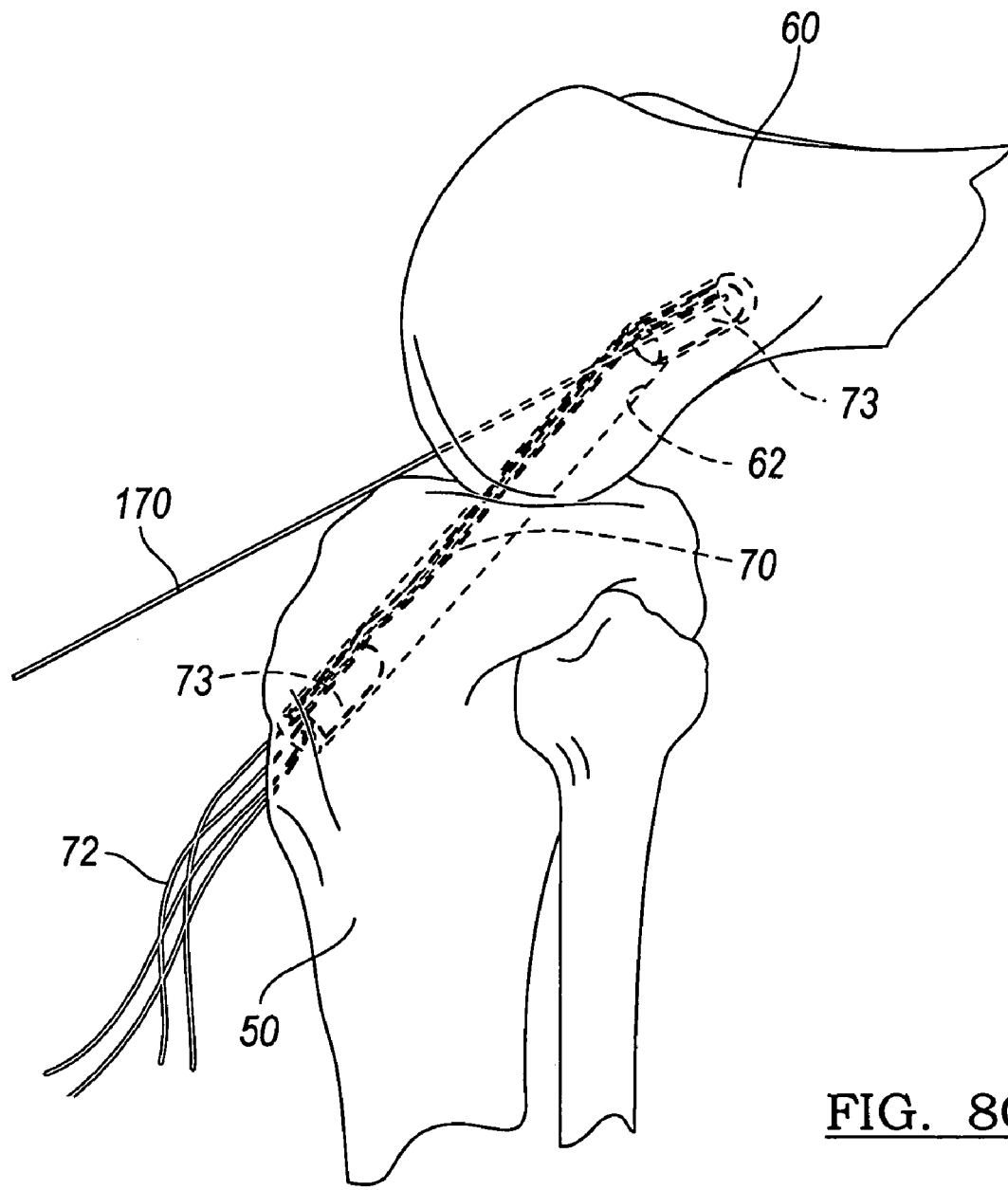

Alternatively, the fixation device 100 can be implanted in the femoral tunnel 62, similarly to the method described above, using a bone-tendon-bone (BTB) graft method in which the graft 70 is provided with bone blocks 73 at each end as shown in FIG. 8G. In this method, for example, the middle third segment of the patellar tendon is excided with attached bone blocks at each end. After the graft 70 with the bone block 73 attached thereon is inserted into the femoral tunnel 62 is fully seated in the femoral tunnel 62, the guide wire 170 is inserted into the femoral tunnel 62 adjacent to the bone block 73 and the fixation device 100 is inserted is described above with reference to FIGS. 8 and 8A-F to secure the graft 70 inside the femoral tunnel 62. The use of the guide wire 170 is optional.

Osteoinductive/conductive material can be optionally injected through the passage 115 of the anchor 102 using, for example, the cannulated driver 160, a syringe, a pump or other suitable delivery device before inserting the plug 150. Alternatively, osteoinductive/conductive material can be used to form the plug 150 which can be pushed into the passage 115 of the anchor 102. The plug 150 can also be in the form of a gel or other biological or biocompatible material, and may have properties promoting tissue growth.

Figure 9:
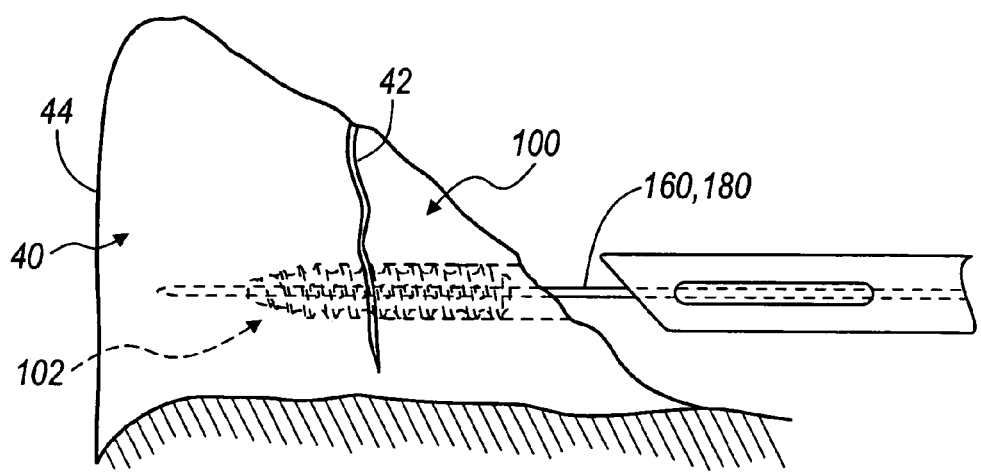
FIG. 9 is an environmental view of a fixation device according to the present teachings.

Referring to FIG. 9, another exemplary use of the fixation device 100 is illustrated in the context of soft tissue repair, such as repairing a meniscus 40 having a tear or other defect 42. The cannulated anchor 102 can be inserted through the defect 42 using an insertion tool, such as drivers 160, 180 as described above. A core or plug, such as a solid or cannulated plug similar to the plug 150 illustrated in FIG. 6, can also be optionally inserted into the passage 115 of the anchor 102. The core can also be in the form of a gel or other biocompatible material, and may have properties promoting tissue growth. The anchor 102 can also be guided through and past the defect 42 such that the anchor exits completely through a back surface 44 of the meniscus 40.

Figure 10:
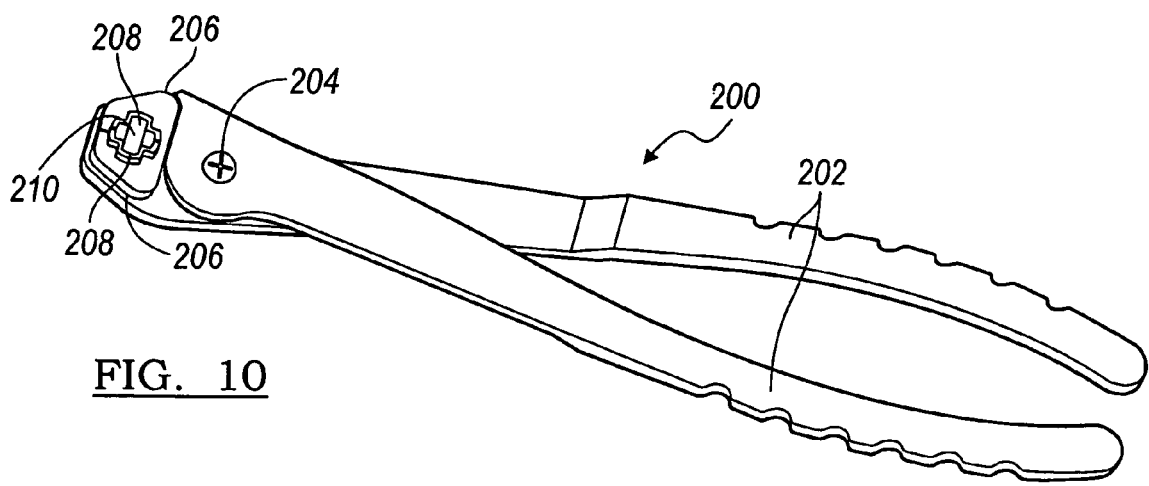
FIG. 10 is a perspective view of a compression instrument for use with a fixation device according to the present teachings.

Referring to FIG. 10, a compression instrument 200 can be provided to enable the operating surgeon to compress autograft or allograft material for the plug 150 into a cruciate or other shape conforming to the plug-receiving portion 116 of the fixation anchor 102. The compression instrument 200 can be a crimper-like instrument having two handles 202 pivotably connected about a pivot 204. The compression instrument 200 can include two jaws 206 that can move between open and closed positions by operation of the handles 202. Each jaw 206 can be provided with an internal face 208 that is configured as one half of the cruciate or other shape that corresponds to the plug 150, such that when the jaws 206 are fully closed the internal faces 208 define a channel 210 that conforms to the external shape of the plug 150. A channel 210 of cruciate shape is illustrated in FIG. 10.

Figure 11:
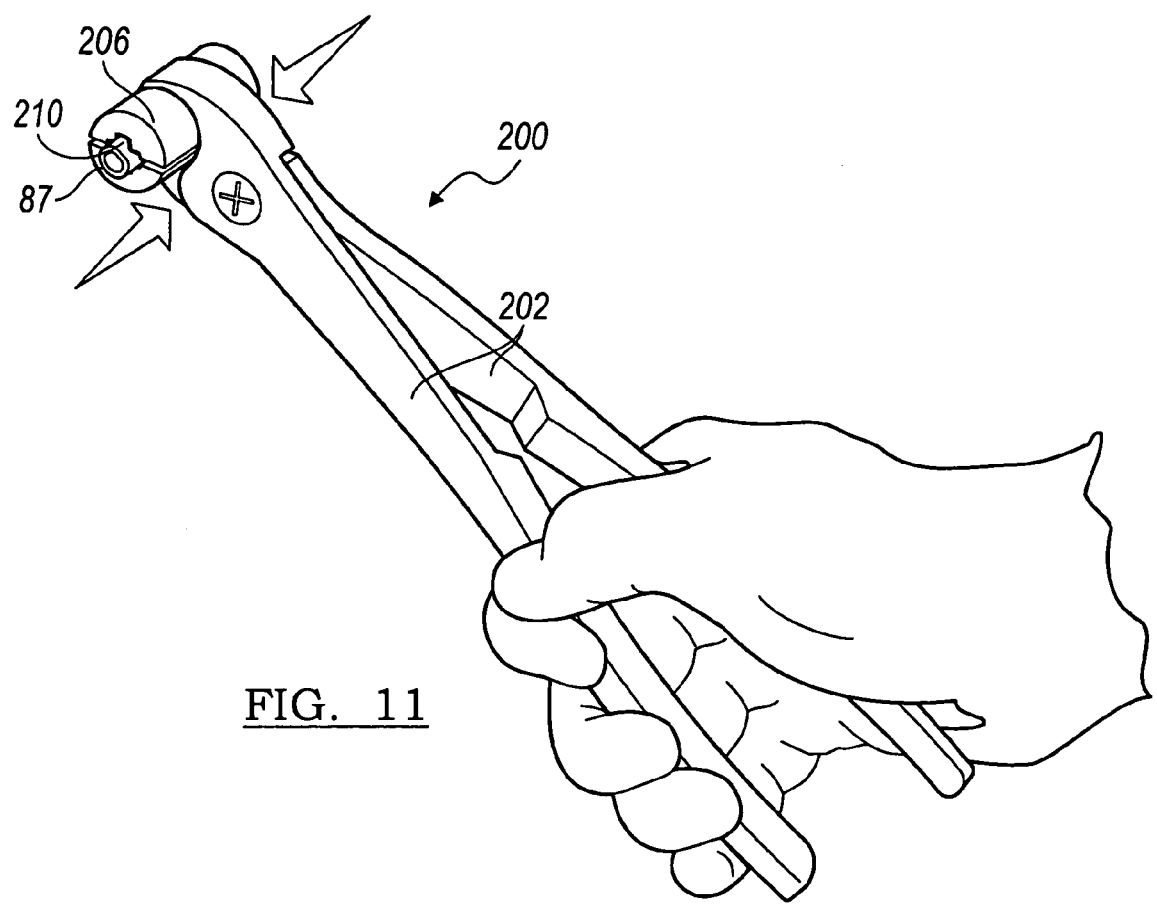
FIGS. 11-13 illustrate aspects of using the compression instrument of FIG. 10 with a harvested bone plug for a fixation device according to the present teachings.
Figure 12:
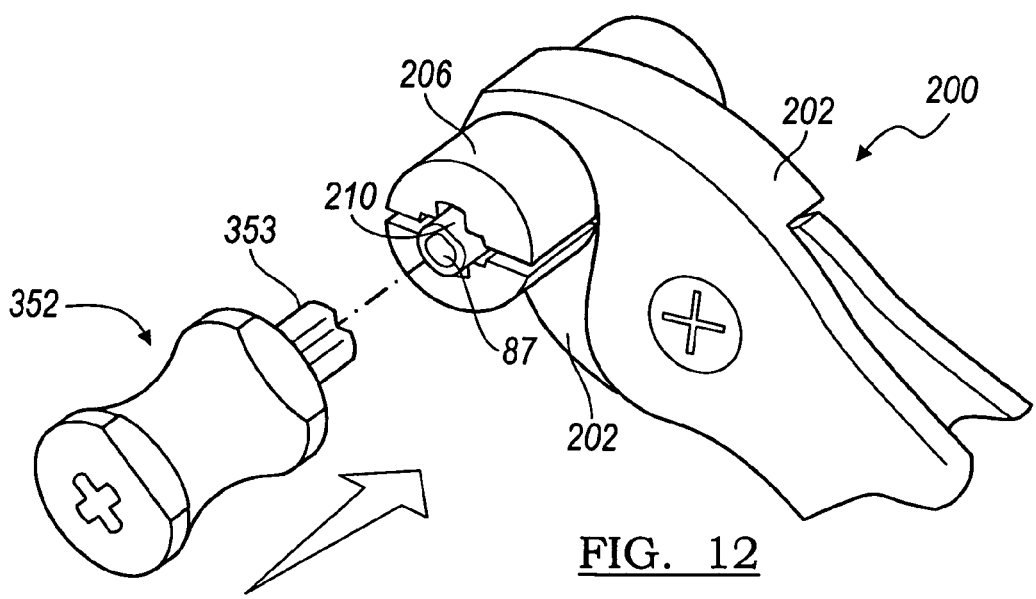
Figure 13:
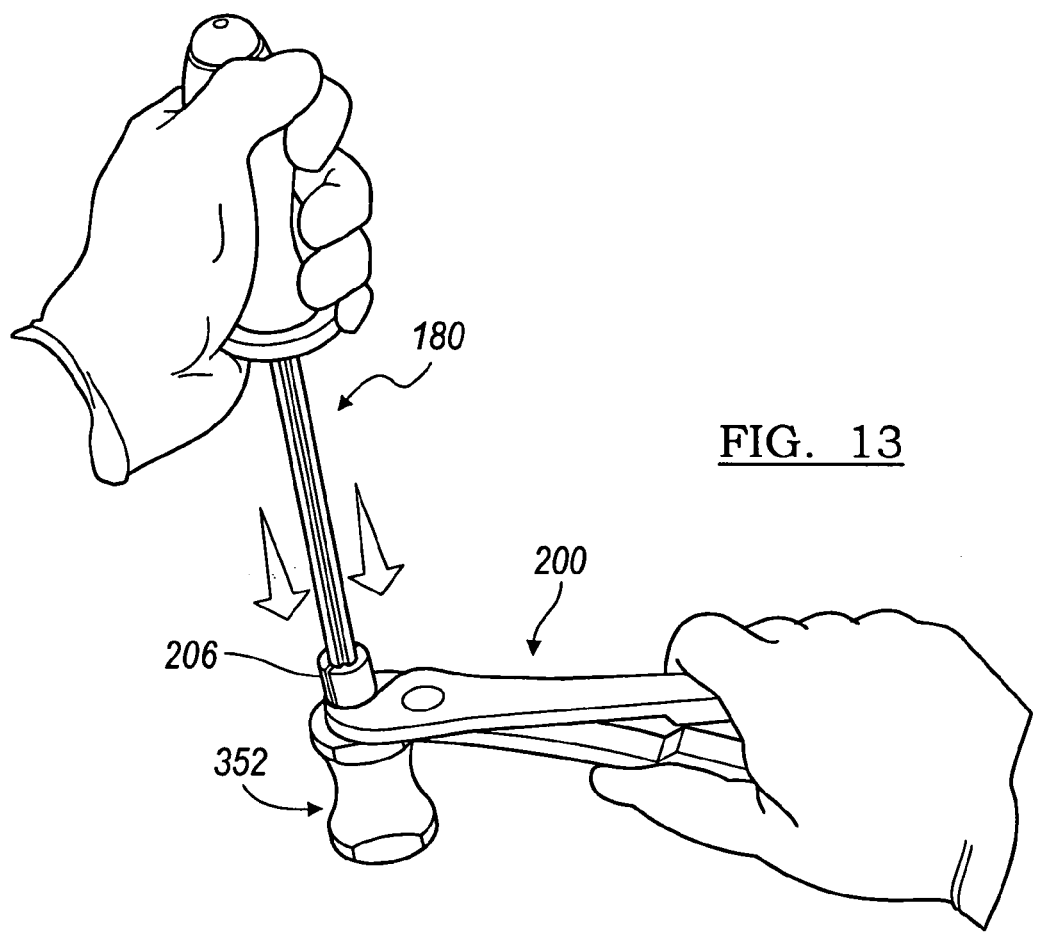

Referring to FIGS. 11-13, the compression instrument 200 can be used to with harvested autograft or allograft bone 87 to prepare the plug 150. The harvested bone 87 is inserted into the channel 210. Pressure can be applied to the handles 202 to crimp or compress the harvested bone 87 into the shape of the plug 150, as shown in FIG. 11. The compactor or plug sleeve 352 can then be mated with the jaws 206 matching the cruciate (or other) shape of an extension 353 of the plug sleeve 352 to the corresponding shape of the channel 210 of the jaws 206, as shown in FIG. 12. The driver 180 can be used to push the bone plug 150 from the channel 210 of the compression instrument 200 into the plug sleeve 352. A mallet can be used to push the driver 180, if needed. The plug sleeve 352 can then be mated with the anchor sleeve 182 as shown in FIG. 8D.

Figure 14:
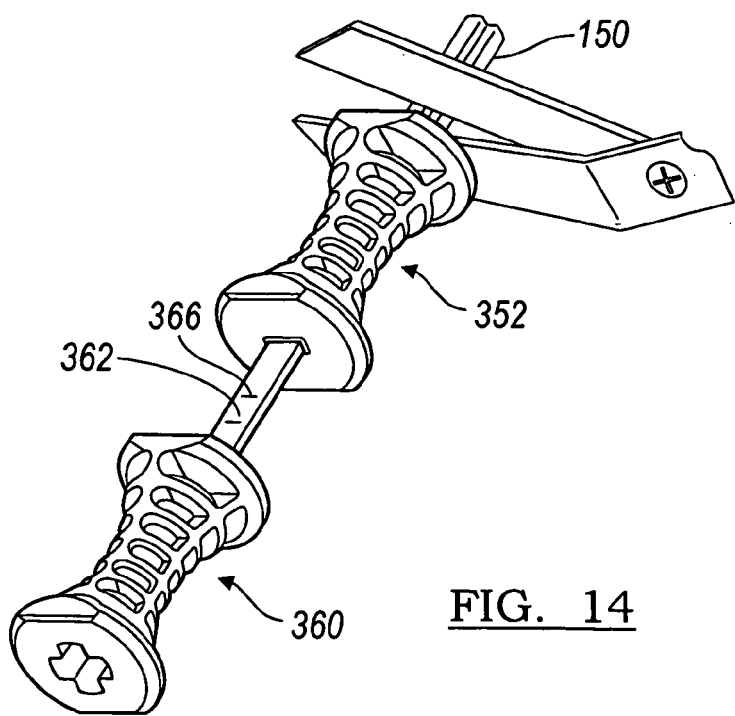
FIGS. 14-16 illustrate aspects of using the compression instrument of FIG. 10 with a pres-shaped DBM plug for a fixation device according to the present teachings.
Figure 15:
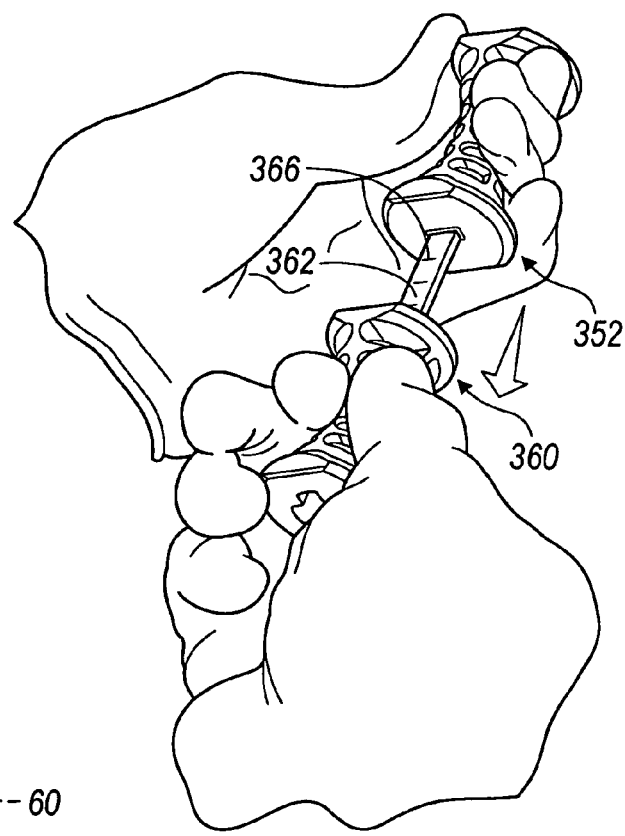
Figure 16:
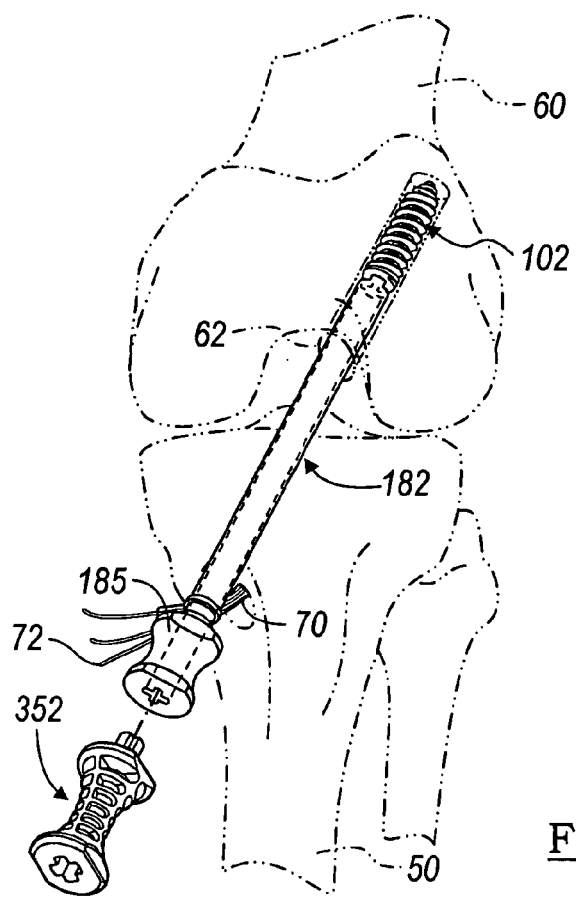

Referring to FIGS. 14-16, the plug 150 can be provided in the form of pre-shaped demineralized bone matrix (DBM) in a pre-assembled package that includes the plug sleeve 352, which can be disposable, made of plastic, for example, and a plug plunger 360. The plug plunger 360 can have a solid shaft 362 with at least a cruciate tip 364 and length markings 366. The plug plunger 360 can be pressed to a line in the markings 366 that corresponds to the size of the fixation anchor 102 used. The pre-shaped plug 150 can be cut flush with the end of the plug plunger 352, as shown in FIG. 16. The plug plunger 360 can be removed from the plug sleeve 352, as shown in FIG. 15, and the plug sleeve 352 can be attached to the back of the anchor sleeve 182, as shown in FIG. 16. The driver 180 can be used to push the plug 150 from the plug sleeve 352 into the anchor sleeve 182 and into the fixation anchor 102, as shown in FIG. 8D.

Figure 17:
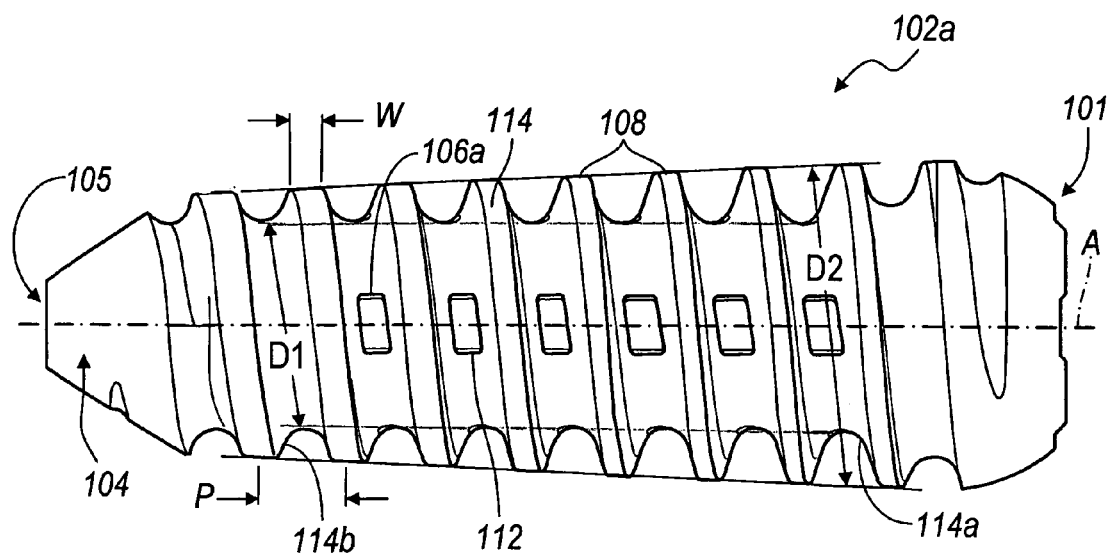
FIG. 17 is a side view of an anchor for a fixation device according to the present teachings.
Figure 18:
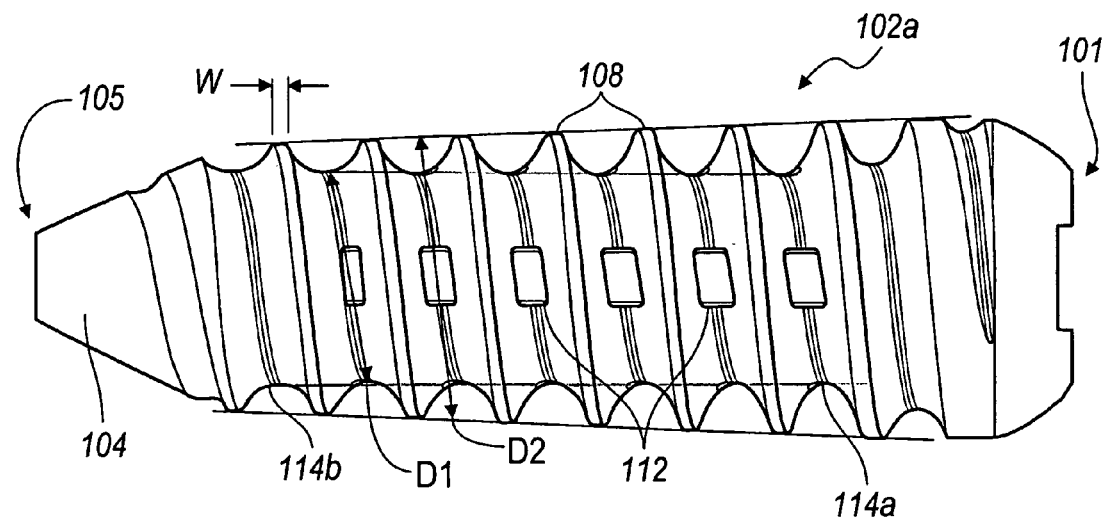
FIG. 18 is a side view of an anchor for a fixation device according to the present teachings.

Referring to FIGS. 17-26, in one aspect, the anchor 102a for the fixation device 100 can have minor thread diameter D1 which is constant along a body portion 106a of the anchor 102, and a major thread diameter D2 which is tapered, such that it decreases continuously along the threaded portion 106 of the anchor 102a from a proximal end 101 of the anchor 102a toward a distal end 105 of the anchor 102. The threads 114 can have constant pitch "p" in the body portion 106a and edges or lands 108 that have increasing width "w" in the direction from the proximal end 101 to the distal end 105, as illustrated in FIG. 17. Alternatively, the lands 108 can have constant width "w" as shown in FIG. 18.

Figure 19:
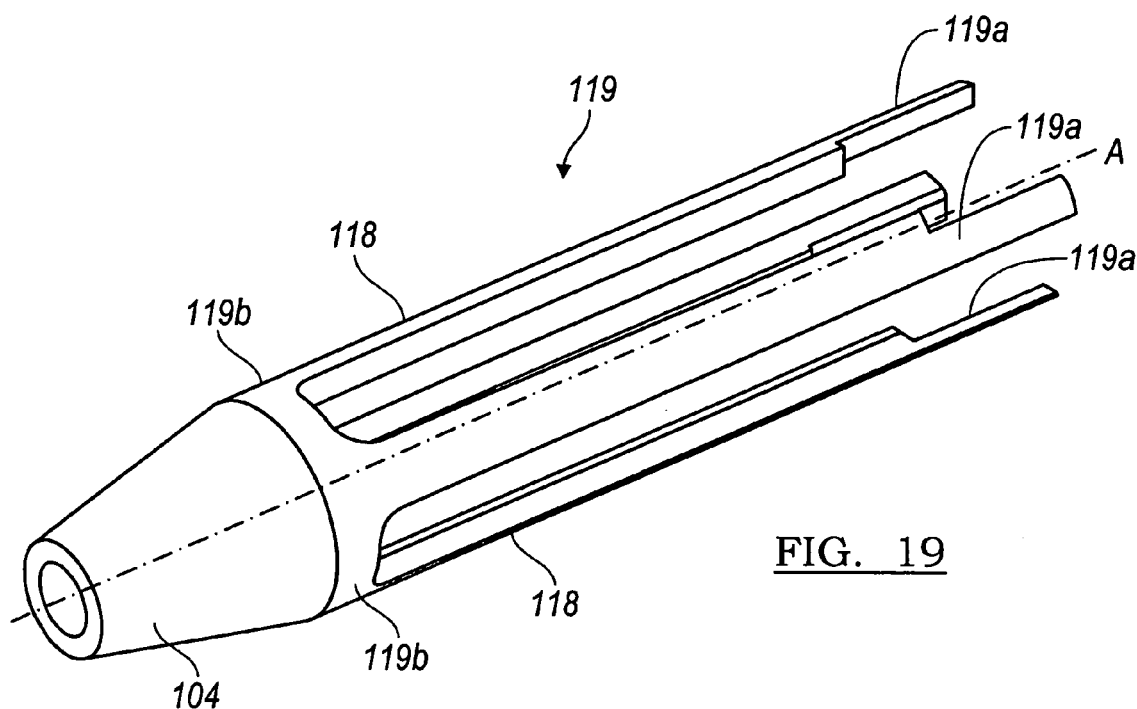
FIG. 19 is a perspective view of a rib structure for an anchor according to the present teachings.
Figure 20:
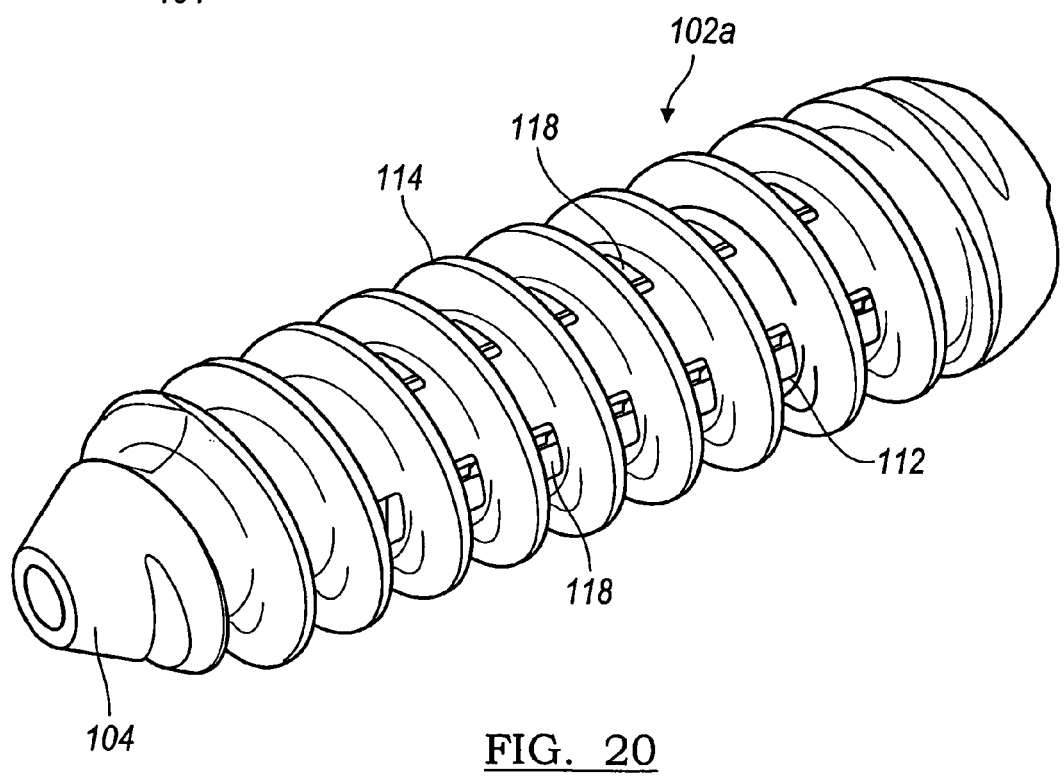
FIG. 20 is a perspective view of an anchor having the rib structure of FIG. 19.

Referring to FIGS. 19 and 20, the anchor 102a can have windows or fenestrations that define apertures 112 between the longitudinal ribs 118 and the threads 114. An illustrative rib structure 119 having four ribs 118 arranged circumferentially about the longitudinal axis A of the anchor 102a is shown in FIG. 19. Each rib 118 has a proximal end 119a and a distal end 119b. The distal ends 119b are attached to the conical tip 104. The proximal ends 119a are configured to allow engagement instruments, such as drivers, inserters or other instruments to interface with the proximal end 101 of the anchor 102a. The threads 114 are then provided on the outside surface of the ribs 118, as illustrated in FIG. 20. In this manner, the ribs 118 provide axial stability to the threads 114, and the threads provide radial stability to the ribs 118. The interdependent load sharing increases the efficiency of the anchor 102 in terms of strength relative to material volume and allows greater volume of biological materials that can be introduced inside the anchor 102.

Figure 21:
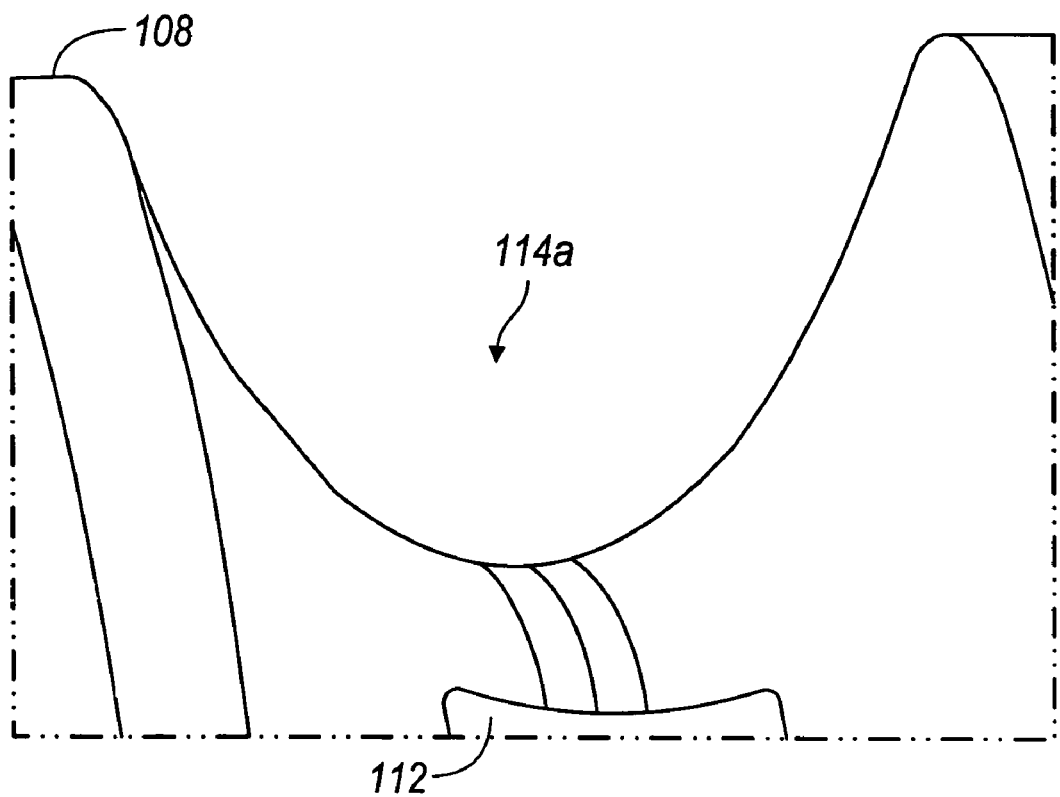
FIG. 21 is an enlarged view of a proximal thread form of the anchor of FIG. 18.
Figure 22:
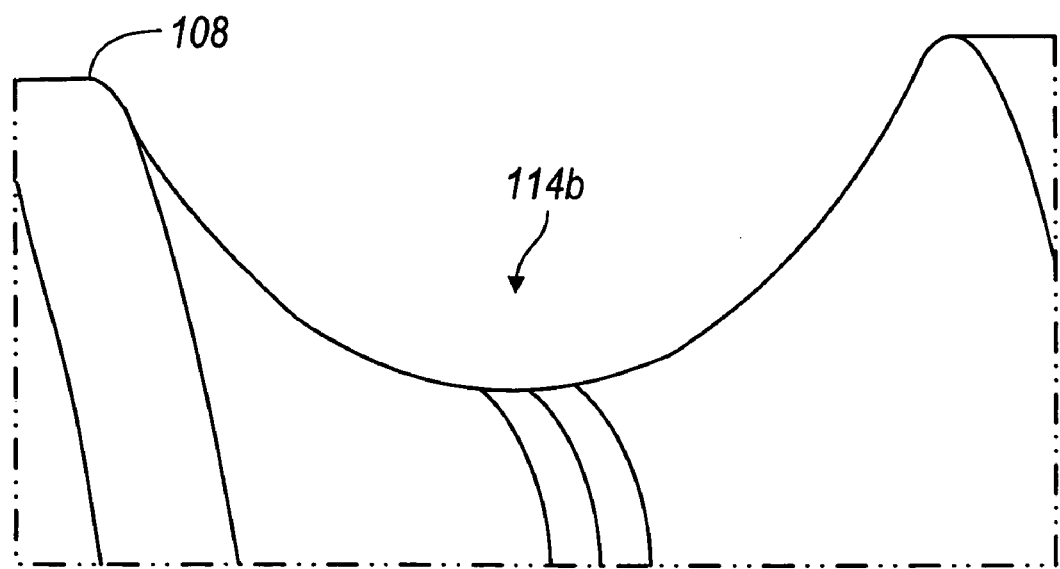
FIG. 22 is an enlarged view of a distal thread form of the anchor of FIG. 18.
Figure 23:
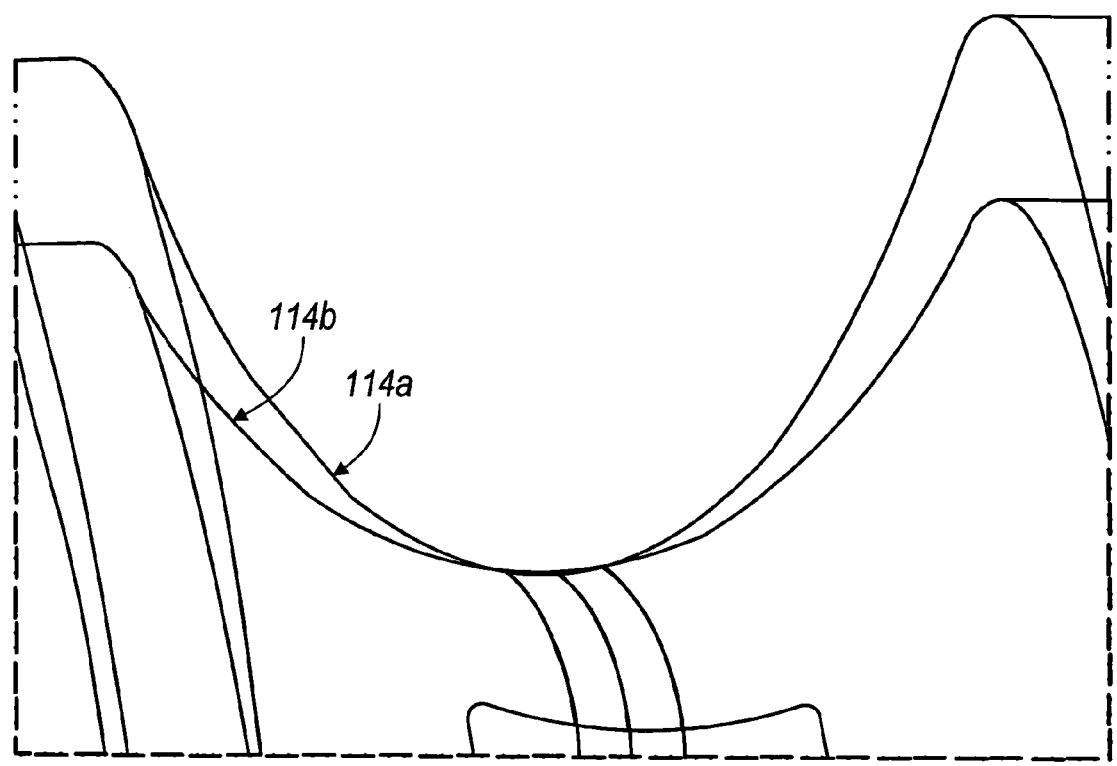
FIG. 23 is a view showing the proximal and distal thread forms of FIGS. 21 and 22 superposed.

Referring to FIGS. 21-23, enlarged views of proximal and distal thread form 114a, 114b of the anchor 102a of FIG. 18 are illustrated. The width of the land 108, the pitch p and the minor thread diameter D1 are constant. FIG. 23 shows the proximal and distal thread forms 114a, 114b superposed for comparison, showing the difference in the shape of the proximal and distal thread forms 114a, 114b.

Figure 24:
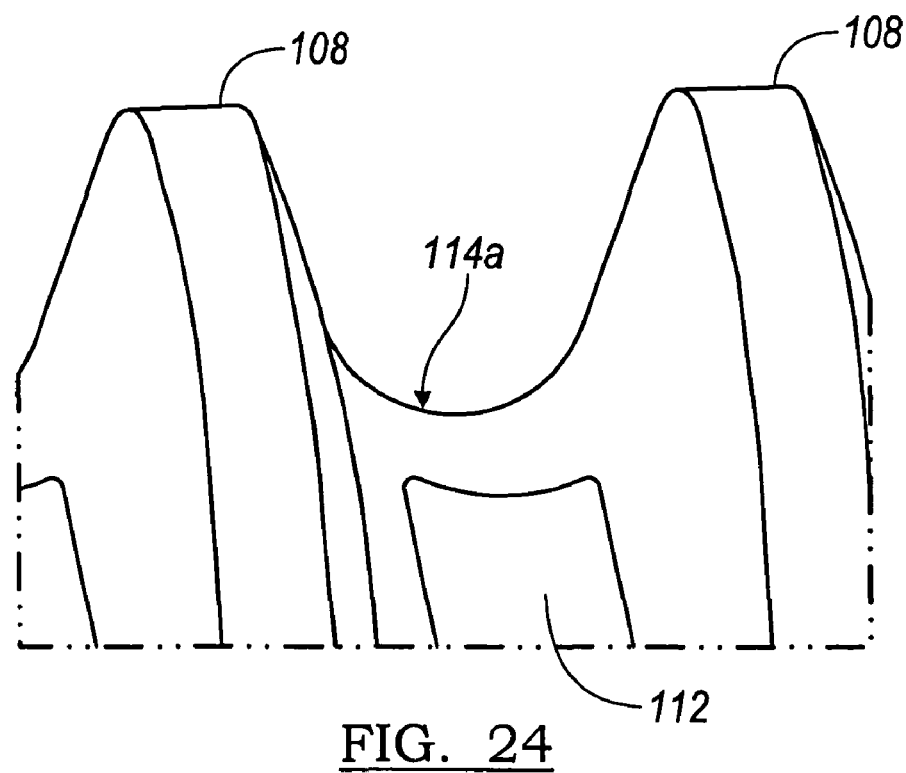
FIG. 24 is an enlarged view of a proximal thread form of the anchor of FIG. 17.
Figure 25:
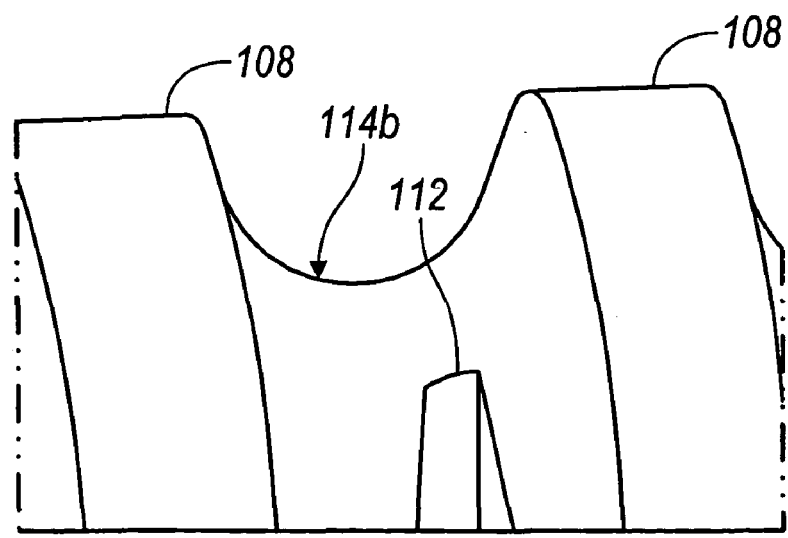
FIG. 25 is an enlarged view of a distal thread form of the anchor of FIG. 17.
Figure 26:
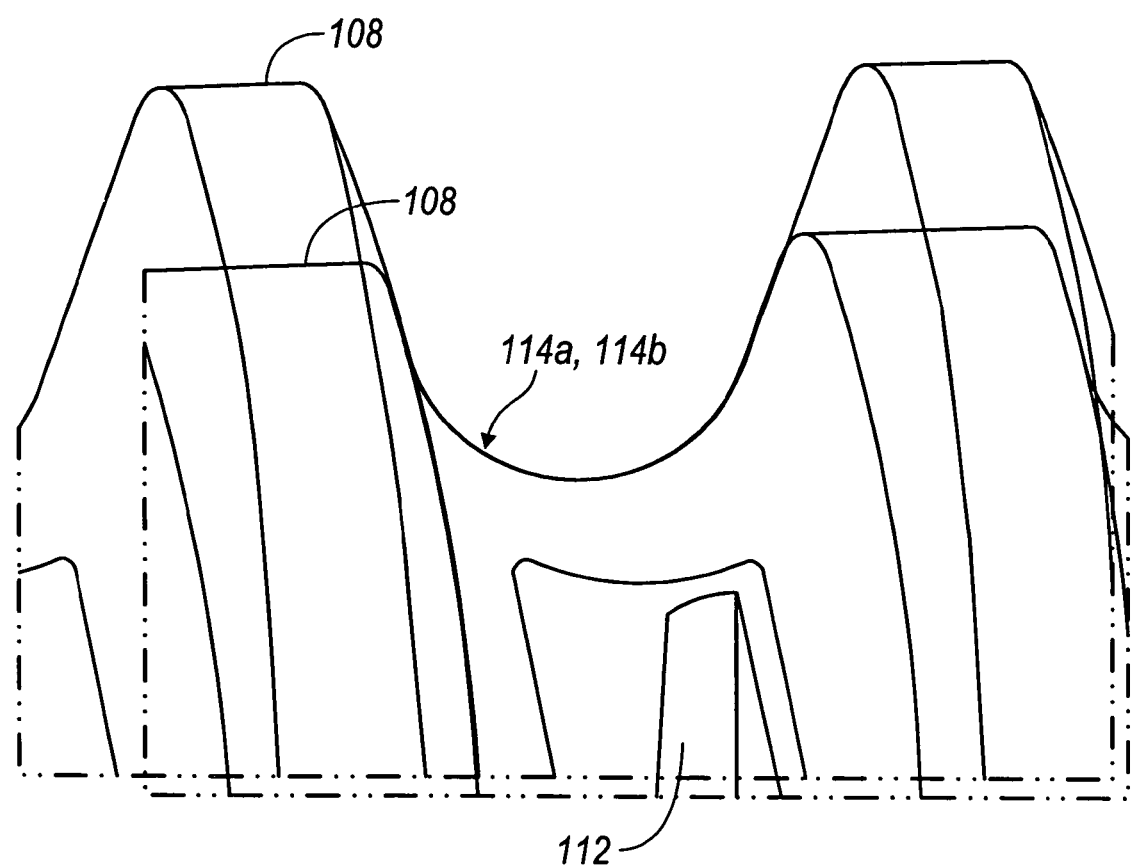
FIG. 26 is a view showing the proximal and distal thread forms of FIGS. 23 and 24 superposed.

Referring to FIGS. 24-26, enlarged views of proximal and distal thread forms 114a, 114b of the anchor 102a of FIG. 17 are illustrated. The width of the land 118 is variable, while the minor diameter D1, the pitch p and the shape the thread form 114a, 114b are constant. FIG. 26 shows the proximal and distal thread forms 114a, 114b superposed for comparison, showing the coincident portions of the proximal and distal thread forms 114a, 114b.

It will be understood that the anchors 102a, 102b of FIGS. 17-26 can include any of the other features of the anchors 102, such as resorbable window covers 113, and can be used with the instruments and methods of use discussed above in connection with FIGS. 1-16.

While particular embodiments and aspects have been described in the specification and illustrated in the drawings, it will be understood by those skilled in the art that various changes may be made and equivalents may be substituted for elements thereof without departing from the scope of the invention as defined in the claims. In addition, many modifications may be made to adapt a particular situation or material to the present teachings without departing from the essential scope thereof. Therefore, it is intended that the present teachings are not be limited to the particular embodiments illustrated by the drawings and described in the specification, but that the present teachings will include any embodiments falling within the foregoing description and the appended claims.

What is claimed is:

1. A method for securing a graft to a bone comprising:
   forming a tunnel in the bone;
   positioning the graft in the tunnel;
   attaching a pronged distal end of an elongated tubular anchor sleeve to a mating proximal end of an anchor;
   inserting a driver through the anchor sleeve;
   engaging an inner surface of a cruciate-shaped bore defined in the anchor with a shaft of the driver, the shaft of the driver having a mating cruciate shape;
   applying torque and driving the anchor into the tunnel with the driver while the anchor sleeve is attached to the anchor;
   securing the graft with the anchor;
   removing the driver;
   inserting a pre-compressed harvested bone material having a cruciate cross-section through the anchor sleeve into the bore of the anchor; and
   removing the anchor sleeve after inserting the bone material into the anchor.

2. The method of claim 1, wherein the harvested bone material is autograft or allograft bone.

3. The method of claim 1, wherein securing the graft in the tunnel includes engaging the anchor with a soft tissue portion of the graft.

4. The method of claim 1, wherein securing the graft in the tunnel includes engaging the anchor with a bone portion of the graft.

5. The method of claim 1, further comprising delivering a biological material inserted in the bore of the anchor through apertures formed through an outer surface of the anchor.

6. The method of claim 1, further comprising resorbing portions of the anchor at different rates of resorption.

7. The method of claim 1, further comprising:
   pushing the bone material through the anchor sleeve with the driver.

8. The method of claim 1, wherein forming a tunnel includes forming a tunnel in femoral bone for anterior or posterior cruciate ligament reconstruction.

9. The method of claim 1, wherein the graft is selected from bone-tendon-bone graft, soft tissue graft, natural graft and artificial graft.

10. A method for securing a graft to a bone comprising:
    forming a tunnel in the bone;
    positioning at least a portion of the graft in the tunnel;
    engaging a proximal end of an anchor with a distal end of an elongated tubular anchor sleeve;
    sliding a driver through the anchor sleeve and engaging a cruciate-shaped shaft of the driver to a cruciate-shaped bore defined in the anchor;
    applying torque to the anchor using the driver to drive the anchor into the tunnel while the proximal end of the anchor is engaged to the distal end of the anchor sleeve;
    securing the graft in the tunnel with the anchor;
    removing the driver;
    inserting biological material in the bore of the anchor by passing the biological material through the anchor sleeve; and
    removing the anchor sleeve after inserting the biological material into the anchor.

11. The method of claim 10, further comprising shaping the biological material into a plug having a cruciate shape.

12. The method of claim 11, further comprising pushing the plug through the anchor sleeve with the driver.

13. The method of claim 10, further comprising sliding the anchor sleeve and the driver over a guide wire.

14. The method of claim 10, wherein the distal end of the anchor sleeve is pronged and mates to the proximal end of the anchor.

15. A method for securing a graft to a bone comprising:
    forming a tunnel in the bone;
    positioning a graft in the tunnel;
    engaging a proximal end of an anchor with a distal end of an elongated tubular anchor sleeve;
    passing a driver through the tubular anchor sleeve;
    mateably engaging a shaft of a driver to a bore defined in the anchor;
    applying torque to the anchor using the driver to drive the anchor into the tunnel while the proximal end of the anchor is engaged to the distal end of the anchor sleeve; and
    securing the graft in the tunnel with the anchor.

16. The method of claim 15, further comprising engaging a cruciate-shaped portion of the driver to a cruciate-shaped portion of the bore of the anchor.

17. The method of claim 16, further comprising pushing a cruciate-shaped plug of biological material through the anchor sleeve with the driver into the bore of the anchor.

18. The method of claim 15, wherein the distal end of the anchor sleeve is pronged and mates to the proximal end of the anchor.

* * * * *

UNITED STATES PATENT AND TRADEMARK OFFICE
CERTIFICATE OF CORRECTION

PATENT NO. : 8,034,090 B2  Page 1 of 1
APPLICATION NO. : 11/386071
DATED : October 11, 2011
INVENTOR(S) : Kevin T. Stone et al.

It is certified that error appears in the above-identified patent and that said Letters Patent is hereby corrected as shown below:

Title Page, Item (56) References Cited, U.S. Patent Documents, 1st reference, delete "26,501 A 10/1859 Kendrick et al.".

Title Page, Item (56) References Cited, U.S. Patent Documents, Page 2, col. 1, reference 32, delete "RE26,501 E 12/1968 Kendrick et al.".

Title Page, Item (57) Abstract, Line 7, delete "to" after "into".

Column 1, Lines 38-43, delete second occurrence of duplicate paragraph: The present teachings provide a method for securing a graft to a bone. The method includes forming a tunnel in the bone, positioning at least a portion of the graft in the tunnel, securing the graft in the tunnel with an anchor, shaping biological material into a plug that conforms to a shape of a bore formed in the anchor, and inserting the plug in the bore of the anchor.".

Figure 4:
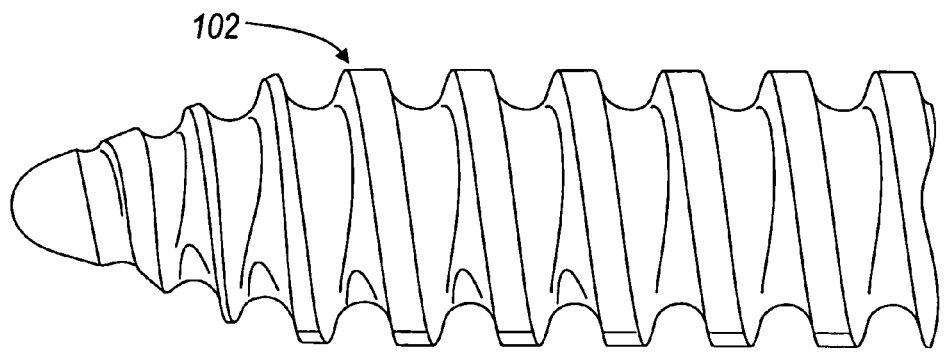
FIG. 4 is a perspective view of an anchor for a fixation device according to the present teachings.
Figure 4A:
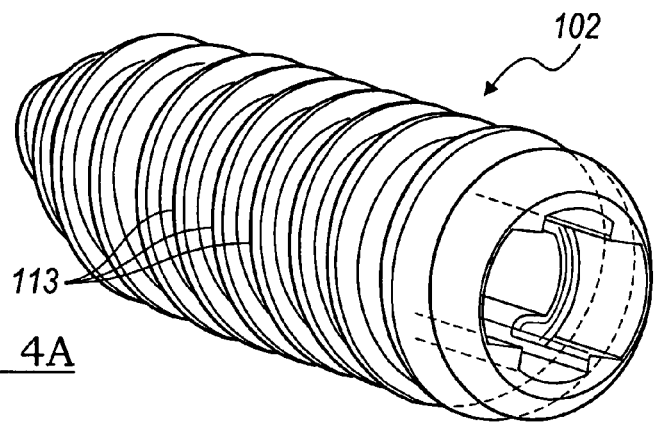
FIG. 4A is a perspective view of an anchor for a fixation device according to the present teachings.
Figure 4B:
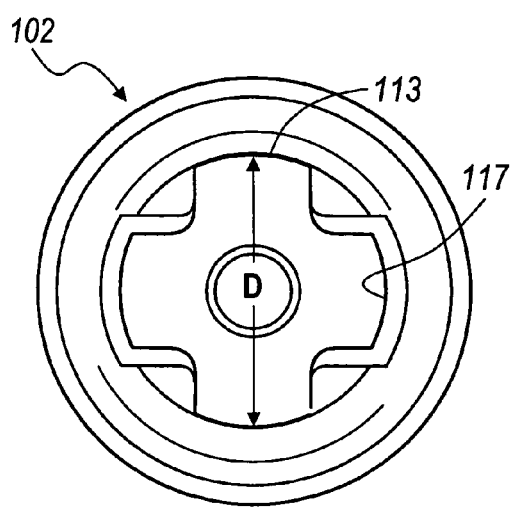
FIG. 4B is an end view of the anchor of FIG. 4A.
Figure 4C:
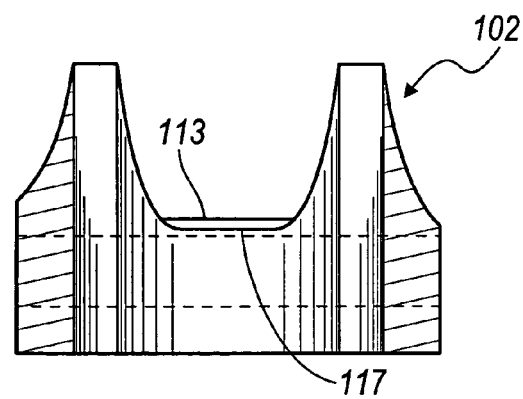
FIG. 4C is a partial side view of the anchor of FIG. 4A.
Figure 4D:
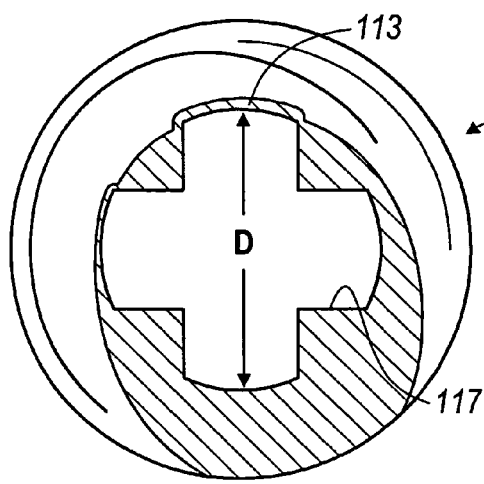
FIG. 4D a cross-sectional view of the anchor of FIG. 4A.
Figure 4E:
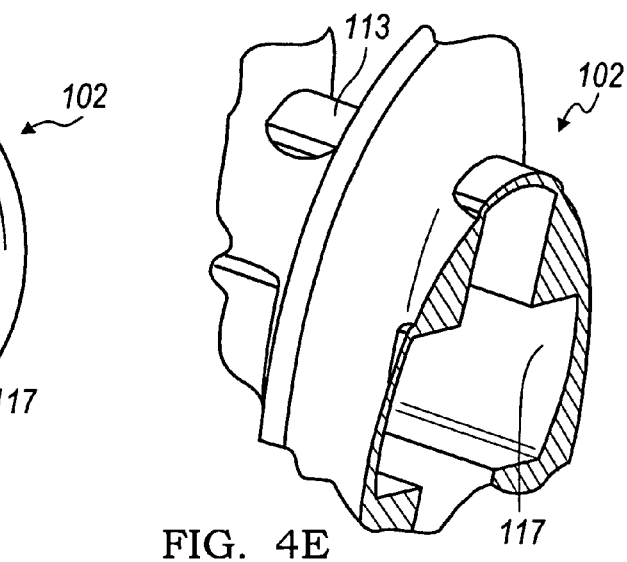
FIG. 4E a detail of the anchor of FIG. 4A.
Figure 5:
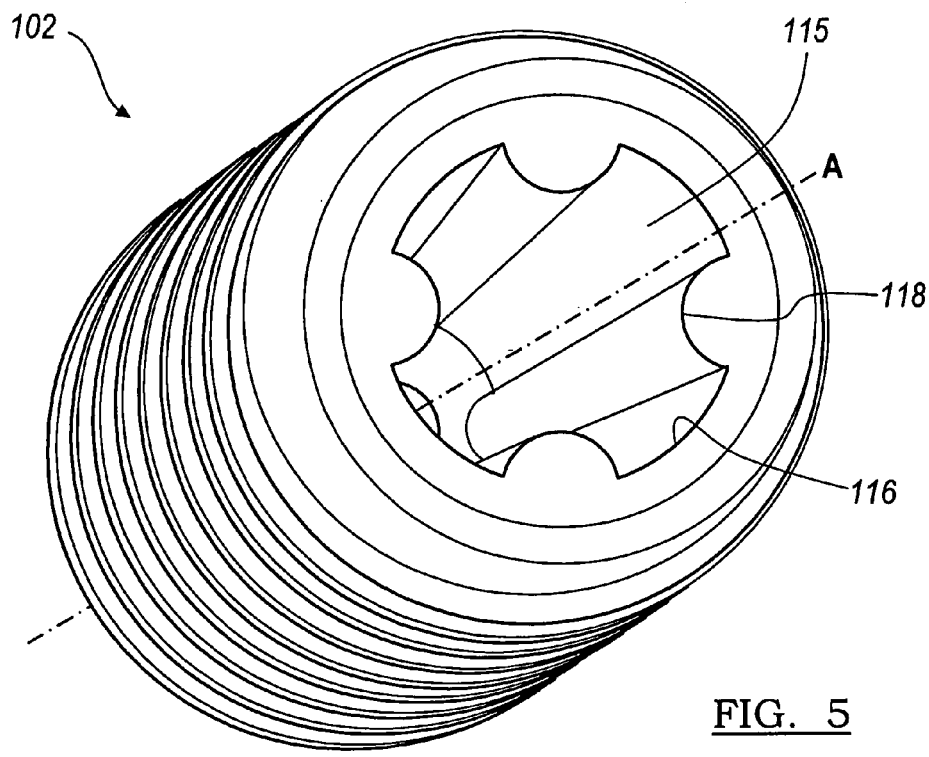
FIG. 5 is a perspective view of an anchor for a fixation device according to the present teachings.
Figure 6:
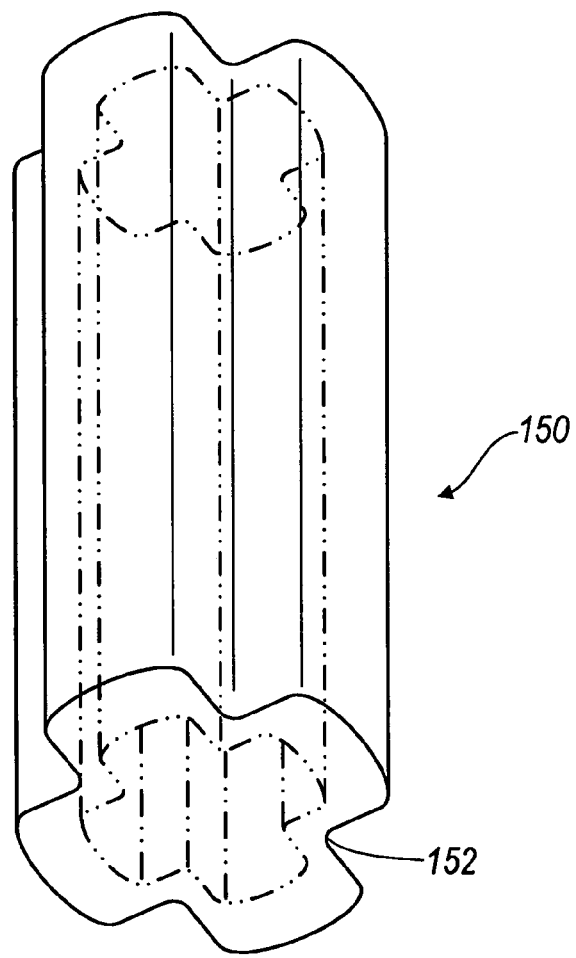
FIG. 6 is a perspective view of a plug for a fixation device according to the present teachings.

Column 2, Line 23, insert --is-- after "FIG. 4D".
Column 2, Line 24, insert --is-- after "FIG. 4E".
Column 2, Line 54, replace "pres-shaped" with --pre-shaped--.
Column 5, Line 35, insert --are-- after "window covers 113".
Column 5, Line 44, replace "FIG. 1, 2 or 3" with --FIGS. 1, 2 or 3--.
Column 6, Line 59, replace "excided" with --excised--.
Column 6, Line 64, replace "inserted is described" with --inserted as described--.
Column 7, Line 39, delete "to" after "used".
Column 8, Line 44, insert --of-- after "shape".
Column 8, Line 64, insert --to-- after "not".

Signed and Sealed this
Twenty-sixth Day of June, 2012

David J. Kappos
*Director of the United States Patent and Trademark Office*